United States Patent [19]

Christensen et al.

[11] Patent Number: 4,725,594

[45] Date of Patent: Feb. 16, 1988

[54] CARBAPENEMS HAVING AN INTERNALLY OR EXTERNALLY ALKYLATED MONO- OR BICYCLIC 2-QUATERNARY HETEROARYLALXYL HETEROMETHYL SUBSTITUENT

[75] Inventors: Burton G. Christensen, Cliffside; James V. Heck, Fanwood; Ronald W. Ratcliffe, Matawan; Thomas N. Salzmann, North Plainfield, all of N.J.

[73] Assignee: Merck & Co., Inc., Rahway, N.J.

[21] Appl. No.: 681,344

[22] Filed: Dec. 13, 1984

[51] Int. Cl.$^4$ .................. C07D 487/04; A61K 31/40
[52] U.S. Cl. ..................................... 514/210; 540/350
[58] Field of Search .................. 260/245.2 T; 514/210

[56] References Cited

U.S. PATENT DOCUMENTS

| | | | |
|---|---|---|---|
| 4,189,493 | 2/1980 | Christensen et al. | 540/350 |
| 4,218,459 | 8/1980 | Cama et al. | 424/274 |
| 4,260,627 | 4/1981 | Christensen et al. | 260/245.2 T |
| 4,262,009 | 4/1981 | Christensen et al. | 260/245.2 T |
| 4,262,011 | 4/1981 | Christensen et al. | 260/245.2 T |
| 4,312,871 | 1/1982 | Christensen et al. | 540/350 |
| 4,341,706 | 7/1982 | Christensen et al. | 540/350 |
| 4,347,355 | 8/1982 | Chu | 542/420 |
| 4,348,320 | 9/1982 | Bouffard et al. | 540/350 |
| 4,377,591 | 3/1983 | Hiraoka et al. | 514/210 |
| 4,465,632 | 8/1984 | Christensen et al. | 540/350 |
| 4,536,335 | 8/1985 | Kim et al. | 260/245.2 T |
| 4,552,696 | 11/1985 | Kim et al. | 260/245.2 T |

FOREIGN PATENT DOCUMENTS

| | | |
|---|---|---|
| 56-60852 | 10/1982 | Japan . |
| 56-199682 | 6/1983 | Japan . |
| 57-145086 | 2/1984 | Japan . |
| 57-145087 | 2/1984 | Japan . |
| 2092147A | 8/1982 | United Kingdom . |
| 2119371A | 11/1983 | United Kingdom . |
| 2122196A | 1/1984 | United Kingdom . |
| 2128187A | 4/1984 | United Kingdom . |

Primary Examiner—Nichols S. Rizzo
Attorney, Agent, or Firm—Raymond M. Speer; Hesna J. Pfeiffer; Robert J. North

[57] ABSTRACT

Carbapenems having the formula:

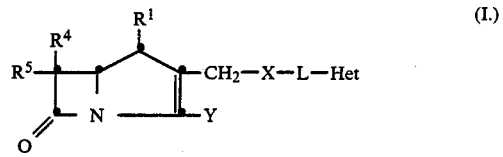

wherein:
$R^1$ is H;
$R^4$ and $R^5$ are independently H, $CH_3-$, $CH_3CH_2-$, $(CH_3)_2CH-$, $HOCH_2-$, $CH_3CH(OH)-$, $(CH_3)_2C(OH)-$, $FCH_2$, $F_2CH-$, $F_3C-$, $CH_3CH(F)-$, $CH_3CF_2-$, $(CH_3)_2C(F)-$; X is $-S-$, $-SO-$, $-SO_2-$, $-O-$ or $-NH$; L is a bridging group comprising substituted or unsubstituted $C_1-C_4$ straight, $C_2-C_6$ branched or $C_3-C_7$ cycloalkyl groups wherein the substituents are selected from $C_1-C_6$ alkyl, $O-C_1-C_6$ alkyl, $S-C_1-C_6$ alkyl, $CF_3$, $N(C_1-C_6$ alkyl$)_2$; Y is a carboxy-containing substituent; Het is internally alkylated heteroarylium, t,20 or externally alkylated heteroarylium,

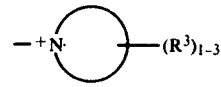

or externally alkylated heteroarylium,

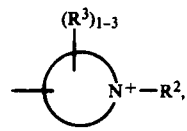

their preparation and antibiotic use are disclosed.

30 Claims, No Drawings

CARBAPENEMS HAVING AN INTERNALLY OR EXTERNALLY ALKYLATED MONO- OR BICYCLIC 2-QUATERNARY HETEROARYLALXYL HETEROMETHYL SUBSTITUENT

BACKGROUND OF THE INVENTION

The present invention is concerned with carbapenem antibiotics having an external or internal quaternary mono- or bicyclic heteroarylalkylthiomethyl group in the 2-position.

Thienamycin is a known carbapenem, broad spectrum antibiotic of the formula:

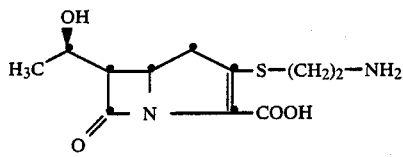

Other derivatives of A are also known.

The present externally or internally alkylated mono- or bicycli 2-quaternary heteroarylalkylthiomethyl substituted carbapenems are believed to have an antibiotic spectrum comparable to A.

BRIEF DESCRIPTION OF DISCLOSES IN THE ART

Sankyo U.S. Pat. No. 4,377,591 and Japanese patent publications 56-199682 and 56-60852 Shionogi Japanese patent publications 57-145086 and 57-145087; and Roche U.K. patent publication No. 2 092 147A, all describe azabicycloheptene antibiotics having a 2-position substituent joined through a thioalkylene bridge. U.S. Pat. No. 4,189,493 to Bristol-Myers discloses externally alkylated heteroarylium alkylthioazabicycloheptene antibiotics. U.S. Pat. No. 4,465,672, U.S. Pat. No. 4,260,627 and U.S. Pat. No. 4,267,188, all assigned to Merck & Co., Inc., disclose 2,6-substituted-1-carba-2-penem-3-carboxylic acids wherein the 2-substituent can be substituted or unsubstituted alkyl or aryl. However, none of the above references specifically describe the carbapenem compounds of the present invention.

SUMMARY OF THE INVENTION

Carbapenems having the formula:

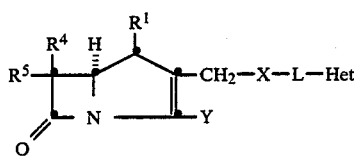

wherein
$R^1$ is H:
$R^4$ and $R^5$ are independently H, $CH_3$—, $CH_3CH_2$—, $(CH_3)_2CH$—, $HOCH_2$—, $CH_3CH(OH)$—, $(CH_3)_2C(OH)$—, $FCH_2$, $F_2CH$—, $F_3C$—, $CH_3CH(F)$—, $CH_3CF_2$—, $(CH_3)_2C(F)$—; X is —S—, —SO—, —SO$_2$—, —O— or —NH; L is a bridging group comprising substituted or unsubstituted $C_1$-$C_4$ straight, $C_3$-$C_6$ branched or $C_3$-$C_7$ cycloalkyl groups wherein the substituents are selected from $C_1$-$C_6$ alkyl, O—$C_1$-$C_6$ alkyl, S—$C_1$-$C_6$ alkyl, $CF_3$, $N(C_1$-$C_6$ alkyl$)_2$;

Y is a carboxy-containing substituent; Het is internally alkylated heteroarylium,

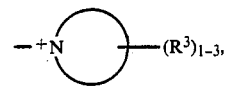

or externally alkylated heteroarylium,

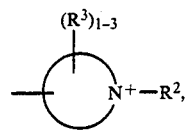

their preparation and antibiotic use are disclosed.

DETAILED DESCRIPTION OF THE INVENTION

The invention is embodied in a compound having the formula:

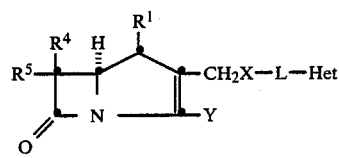

wherein:
$R^1$ is hydrogen;
$R^4$ and $R^5$ are independently H, $CH_3$—, $CH_3CH_2$—, $(CH_3)_2CH$—, $HOCH_2$—, $CH_3CH(OH)$—, $(CH_3)_2C(OH)$—, $FCH_2$, $F_2CH$—, $F_3C$—, $CH_3CH(F)$—, $CH_3CF_2$—, $(CH_3)_2C(F)$—; X is —S—, —SO—, —SO$_2$—, —O— or —NH;
L is a bridging group comprising substituted or unsubstituted $C_1$-$C_4$ straight, $C_2$-$C_6$ branched or $C_3$-$C_7$ cycloalkyl groups wherein the substituents are selected from $C_1$-$C_6$ alkyl, O—$C_1$-$C_6$ alkyl, S—$C_1$-$C_6$ alkyl; $CF_3$, $N(C_1$-$C_6$ alkyl$)_2$;
wherein Het is a mono- or bicyclic heteroarylium group containing from 5-11 ring atoms of which up to 5 are heteroatoms, in addition to the quaternary nitrogen, being

or

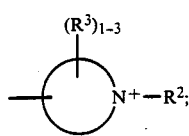

wherein $R^2$ is
(1) an unsubstituted or substituted $C_1$-$C_6$ alkyl radical;
(2) an unsubstituted or substituted $C_2$-$C_6$ alkenyl radical;

(3) an unsubstituted or substituted $C_2$-$C_6$ alkynyl radical;

(4) a $C_3$-$C_7$ cycloalkyl radical in which the ring is substituted or unsubstituted and one or more atoms may be replaced by a heteroatom;

(5) a $C_3$-$C_7$ cycloalkyl methyl radical in which the ring may be substituted and one or more atoms may be replaced by a heteroatom;

(6) an unsubstituted or substituted $C_5$-$C_7$ cycloalkenyl radical;

(7) an unsubstituted or substituted bivalent $C_2$-$C_6$ alkylidene radical, optionally interrupted by a heteroatom, and joined to the heteroarylium group to form a ring which is carbocyclic or in which one or more atoms is replaced by a heteroatom and wherein the new ring may contain one or more double bonds;

(8) an unsubstituted or substituted phenyl or heteroaryl radical;

(9) an unsubstituted or substituted phenyl ($C_1$-$C_4$ alkyl) or heteroaryl ($C_1$-$C_4$ alkyl) or radical;

(10) a cyano ($C_1$-$C_4$ alkyl) radical;

(11) a carboxy ($C_1$-$C_4$ alkyl) radical;

(12) a sulfo ($C_1$-$C_4$ alkyl) radical;

(13) a carbamoyl ($C_1$-$C_4$ alkyl) radical;

(14) a phosphonyl ($C_1$-$C_4$ alkyl) radical;

(15) a hydroxy ($C_1$-$C_4$ alkyl) radical; or

(16) an amino ($C_1$-$C_4$ alkyl) radical in which the nitrogen atom is unsubstituted or substituted with one to three $C_1$-$C_4$ alkyl groups;

wherein the substituents in the above definitions of $R^2$ are independently selected from the group consisting of:

(a) a trifluoromethyl group;

(b) a halogen atom;

(c) an unsubstituted or substituted $C_1$-$C_4$ alkoxy radical;

(d) a hydroxy group;

(e) an unsubstituted or substituted ($C_1$-$C_6$ alkyl) carbonyloxy radical;

(f) a carbamoyloxy radical which is unsubstituted or substituted on nitrogen with one or two $C_1$-$C_4$ alkyl groups;

(g) a $C_1$-$C_6$ alkylthio radical, $C_1$-$C_6$ alkylsulfinyl radical or $C_1$-$C_6$ alkylsulfonyl radical, each of which is unsubstituted or substituted on the alkyl group;

(h) a sulfo group;

(i) a sulfamoyl group which is unsubstituted or substituted on nitrogen by one or two $C_1$-$C_4$ alkyl groups;

(ia) an amino group;

(ib) a mono ($C_1$-$C_4$ alkyl) amino or di($C_1$-$C_4$ alkyl) amino group, each of which is unsubstituted or substituted on the alkyl group;

(j) a formylamino group;

(k) an unsubstituted or substituted ($C_1$-$C_6$ alkyl)-carbonylamino radical;

(l) a ($C_1$-$C_4$ alkoxyl) carbonylamino radical;

(m) a ureido group in which the terminal nitrogen is unsubstituted or substituted with one or two $C_1$-$C_4$ alkyl groups;

(n) an arylsulfonamido or a ($C_1$-$C_6$ alkyl)sulfonamido group;

(o) a cyano group;

(p) a formyl or acetalized formyl radical;

(q) an unsubstituted or substituted ($C_1$-$C_6$ alkyl)-carbonyl radical wherein the carbonyl is free or acetalized;

(r) an unsubstituted or substituted phenylcarbonyl or heteroarylcarbonyl radical;

(ra) a hydroximinomrthyl radical in which the oxygen or carbon atom is optionally substituted by a $C_1$-$C_4$ alkyl group;

(s) a carboxyl group;

(t) a ($C_1$-$C_6$ alkoxy)carbonyl radical;

(u) a carbamoyl radical which is unsubstituted or substituted on nitrogen by one or two $C_1$-$C_4$ alkyl groups;

(v) an N-hydroxycarbamoyl or N($C_1$-$C_4$ alkoxy)-carbamoyl radical in which the nitrogen atom may be additionally substituted by a $C_1$-$C_4$ alkyl group;

(w) a thiocarbamoyl group;

(x) a 5-(1H)-tetrazolyl group;

(xa) an amidino group

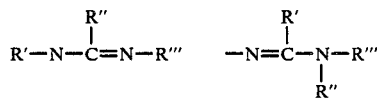

(xb) a carboxamidino group

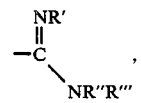

where R', R'' and R''' are as defined above;

(xc) a guanidinyl group where R'' in (ab) above is $NR^{iv}R^v$ and $R^{iv}$ and $R^v$ are as defined for R' through R''' above;

(y) a phosphonate group —P(O) (O$^-$)OR' where R' is $C_1$-$C_3$alkyl;

(z) an alkyl phosphonate group —(CH$_2$)$_n$P(O) (O$^-$) (OR') where n=1 to 3 and R' is $C_1$-$C_3$alkyl;

(aa) hydrogen;

(ab) an unsubstituted or substituted $C_1$-$C_6$ alkyl radical;

(ac) an unsubstituted or substituted $C_2$-$C_6$ alkenyl radical;

(ad) an unsubstituted or substituted $C_2$-$C_6$ alkynyl radical;

(ae) a $C_3$-$C_7$ cycloalkyl radical in which the ring is substituted or unsubstituted and one or more atoms may be replaced by a heteroatom;

(af) a $C_3$-$C_7$ cycloalkyl methyl radical in which the ring may be substituted and one or more atoms may be replaced by a heteroatom;

(ag) an unsubstituted or substituted $C_5$-$C_7$ cycloalkenyl radical;

(ah) an unsubstituted or substituted phenyl or heteroaryl radical; and (ai) an unsubstituted or substituted phenyl ($C_1$-$C_4$ alkyl) or heteroaryl ($C_1$-$C_4$ alkyl) radical; and $R^3$ is (a) hydrogen;

(b) an unsubstitued or substituted $C_1$-$C_6$ alkyl radical;

(c) an unsubstituted or substituted $C_2$-$C_6$ alkenyl radical;

(d) an unsubstituted or substituted $C_2$-$C_6$ alkynyl radical;

(e) a $C_3$–$C_7$ cycloalkyl radical in which the ring is substituted or unsubstituted and one or more atoms may be replaced by a heteroatom;

(f) a $C_3$–$C_7$ cycloalkyl methyl radical in which the ring may be substituted and one or more atoms may be replaced by a heteroatom;

(g) an unsubstituted or substituted $C_5$–$C_7$ cycloalkyl radical;

(h) an unsubstituted or substituted phenyl or heteroaryl radical;

(i) an unsubstituted or substituted phenyl ($C_1$–$C_4$ alkyl) or heteroaryl ($C_1$–$C_4$ alkyl) radical; and (j) a trifluoromethyl group;

(k) a halogen atom;

(l) an unsubstituted or substituted $C_1$–$C_4$ alkoxyl radical;

(m) a $C_1$–$C_6$ alkylthio radical, $C_1$–$C_6$ alkylsulfinyl radical or $C_1$–$C_6$ alkylsulfonyl radical, each of which is unsubstituted or substituted on the alkyl group;

(n) a mono ($C_1$–$C_4$ alkyl) amino or di($C_1$–$C_4$ alkyl)amino group, each of which is unsubstituted or substituted on the alkyl group; or (i) a cyano group; and Y is (i) COOH or a pharmaceutically acceptable ester or salt thereof, (ii) COOR wherein R is a removable carboxy protecting group, such as p-nitrobenzyl, benzyl or allyl, (iii) COOM wherein M is an alkali metal, or (iv) $COO^-$; provided that when Y is other than (iv) a counterion $Z^-$ is provided.

As used herein, the term "heteroatom" means nitrogen, oxygen, or sulfur, independently selected where more than one heteroatom is involved.

Representative L groups are substituted or unsubstituted branched or linear $C_1$–$C_4$ alkyl and include —$CH_2$—, —$CH(CH_3)$—, —$CH(C_2H_5)$—, —$(CH_2)_{2-4}$, —$CH(CH_3)$—$CH_2$—, $CH_2$—$CH(OCH_3)$—, —$CH(CH_3)$—$(CH_2)_2$—, —$CH(CH_2OH)$—$CH_2$—, —$CH(CF_3)$—$CH_2$—, and the like.

Preferred L groups are —$CH_2$—, —$CH(CH_3)$—, —$(CH_2)_2$—, and —$CH(CH_3)CH_2$—.

Examples of useful $R^2$ groups are —$CH_3$, —$(CH_2)_{1-3}$—$CH_3$,

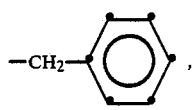

—$(CH_2)_{1-3}$—O—$CH_3$, —$CH_2$—CN, $CH_2$—$COOC_1$–$C_3$ alkyl, —$(CH_2)_2$—N($C_1$–$C_3$ alkyl)$_2$, —$CH_2$—COOH(Na), —$(CH_2)_2$—$SO_3$H(Na),

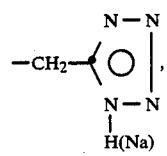

$CH_2CONH_2$, —$(CH_2)_2$—$N^+(CH_3)_3$ and the like.

Preferred $R^2$ groups are the $C_1$–$C_6$ alkyls, both substituted and unsubstituted, carboxy ($C_1$–$C_4$ alkyl), carbamoyl ($C_1$–$C_4$ alkyl), sulfo ($C_1$–$C_4$ alkyl), heteroaryl ($C_1$–$C_4$ alkyl) or cyano ($C_1$–$C_4$ alkyl).

Preferred substituents are CN, CON($CH_3$)$_2$, $CONH_2$, $SOCH_3$, $SO_2CH_3$, $CO_2H$, $SO_3H$, $SO_2NH_2$ and

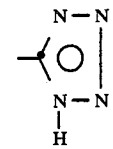

Examples of useful $R^3$ groups are hydrogen, N($C_1$–$C_3$alkyl), $OC_1$–$C_4$alkyl, $C_1$–$C_4$alkyl, CN, $CF_3$, $CH_2OH$ and the like.

Preferred $R^3$ groups are H, —$CH_3$, —$OCH_3$, CN, —$SO_2CH_3$, $CH_2CN$, and the like.

Preferred $R^4$ and $R^5$ groups are where $R^4$ is hydrogen and $R^5$ is

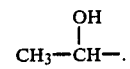

The

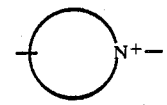

moiety is mono- or bicyclic quaternary heteroarylium group having 5–11 ring atoms of which, in addition to the quaternary $N^+$, up to four can be heteroatoms.

Representative

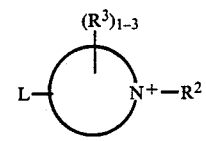

groups are:

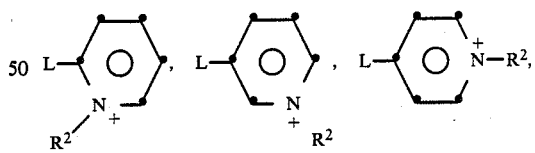

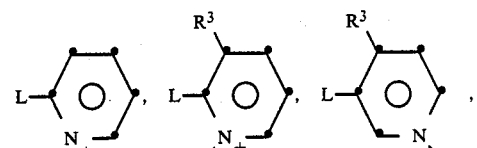

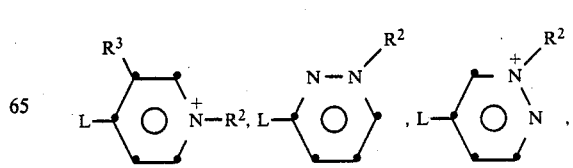

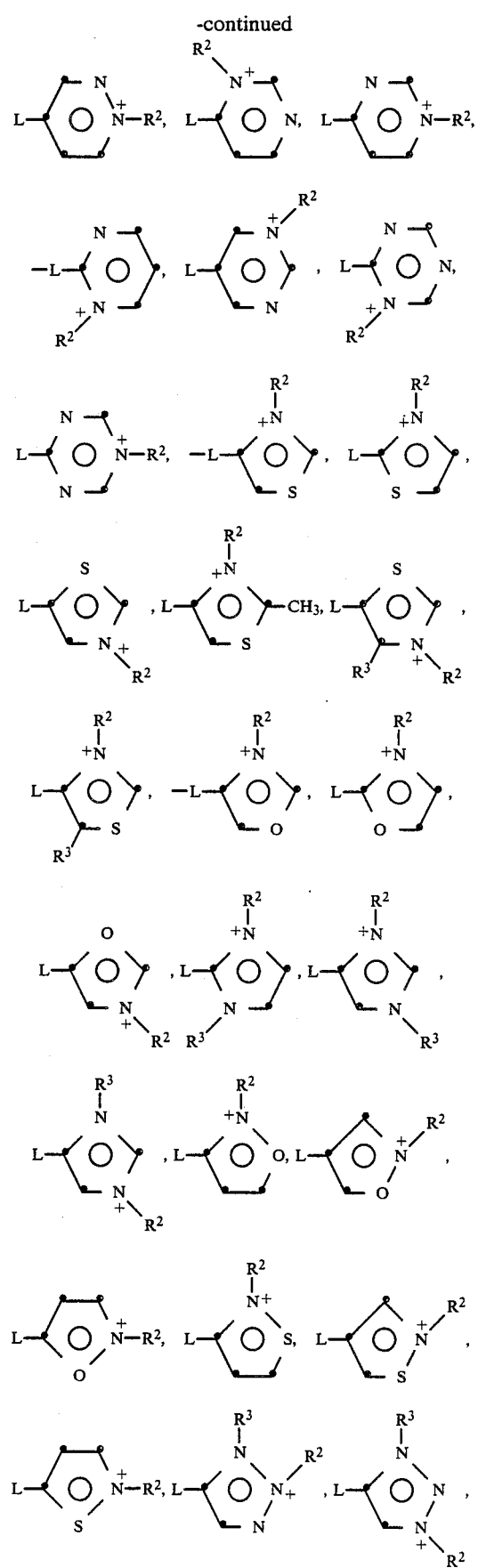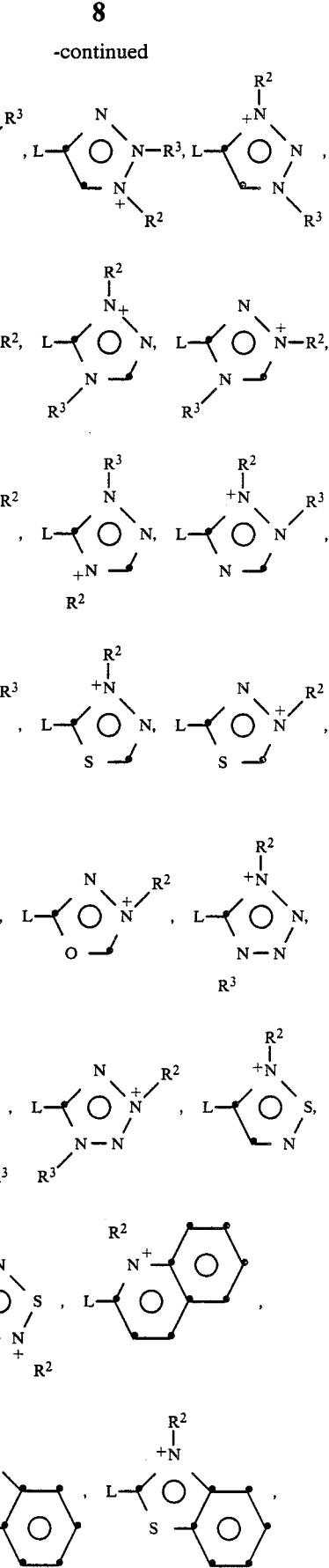

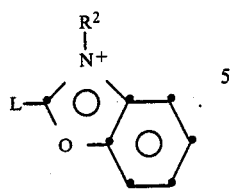

A preferred

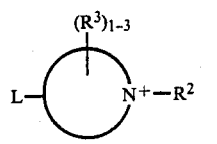

group is monocyclic heteroarylium having 5-6 ring atoms and optionally one heteroatom additional to the N atom already present, e.g.,

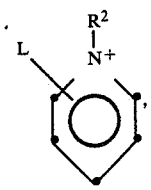 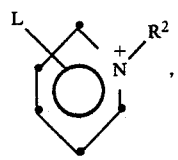,

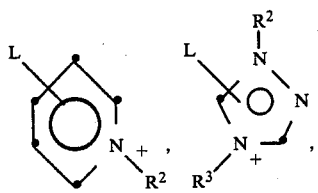,

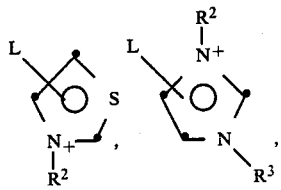,

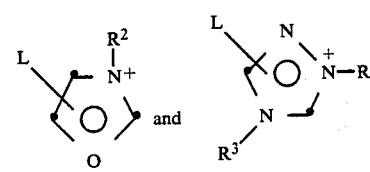 and where $R^2$ and $R^3$ are as defined in the preferred list above and L is —CH$_2$— or —CH$_2$CH$_2$—.

An especially preferred subclass includes the nuclei shown above where $R^3$ (where present) is —CH$_3$, L is —CH$_2$— or —CH$_2$CH$_2$— and $R^2$ is C$_1$–C$_6$ alkyl, unsubstituted or substituted by —CN, —CON(CH$_3$)$_2$, —CONH$_2$, —SOCH$_3$, —SO$_2$CH$_3$, —CO$_2$H, —CO$_2^-$, —SO$_3$H, —SO$_2$NH$_2$ and

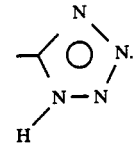

Further preferred compounds of Formula I include those where $R^1$ is H or CH$_3$ and

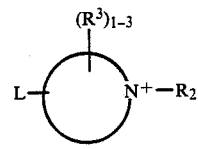

is

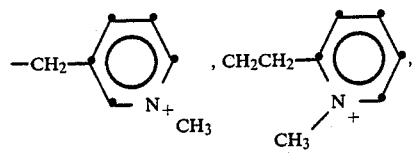

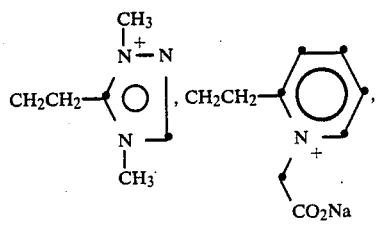

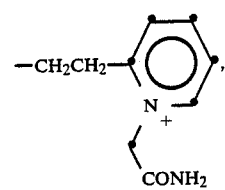

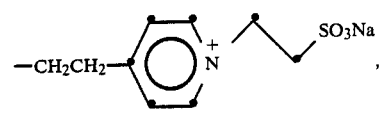

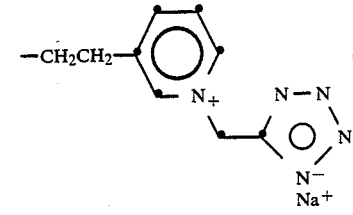

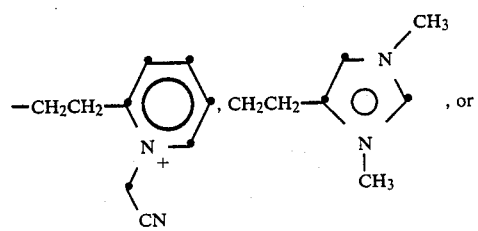

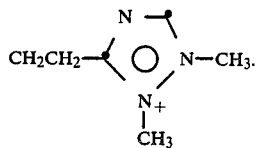

The compounds of Formula I include inner (Zwitterion) salts when Y is COO⁻ e.g.

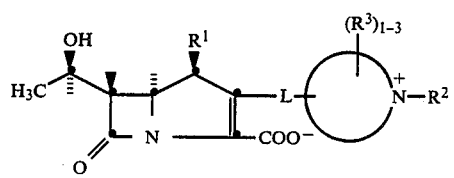

or, when Y is other than COO⁻, salts with an external, physiologically acceptable counterion Z⁻ such as Cl⁻, Br⁻, I⁻, OCH$_3$⁻, OSO$_2$CF$_3$⁻, OP(O) (O phenyl)$_2$⁻ and the like.

The inner salts are preferred.

Again, the compounds of Formula I include the stereoisomers as mixtures and as separate isomers.

A preferred isomer configuration is:

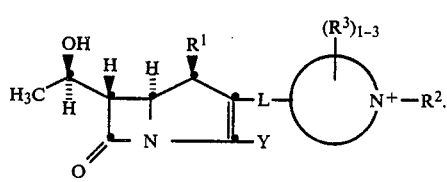

(Ia)

Representative useful internally alkylated monocyclic

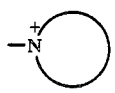

groups are substituted and unsubstituted pyridinium, pyridazinium, pyrimidinium, pyrazinium, pyrazolium, triazolium, imidiazolium, thiazolium, oxazolium and the like.

Preferred Formula I compounds internally alkylated are those where monocyclic

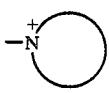

is a six membered heterocycle, such as substituted or unsubstituted pyridinium, pyridazinium or pyrazinium, and preferably substituted or unsubstituted pyridinium, wherein the substituents (one or more) are selected from OH, NH$_2$, NHCH$_3$, OCH$_3$, COO—C$_1$-C$_3$ alkyl, C(O)NHOH, phenyl, N(CH$_3$)$_2$, C(O)CH$_3$, C(O)N(CH$_3$)OH, SO$_3$H, SCH$_3$, CHO, COOH, S(O)CH$_3$, SO$_2$CH$_3$, SO$_2$NH$_2$, SO$_2$NHCH$_3$, SO$_2$CH$_3$, CN, C$_5$NH$_2$, CONH$_2$, CONH(CH$_3$), CH=N—OH, C$_1$-C$_6$ alkenyl and substituted and unsubstituted C$_1$-C$_6$ alkyl.

The preferred substituents are unsubstituted C$_1$-C$_6$ alkyl, C$_1$-C$_6$ alkenyl, and substituted C$_1$-C$_6$ alkyl wherein the substituents (one or more) are selected from OH, NH$_2$, NHCH$_3$, OCH$_3$, —COO—C$_1$-C$_3$alkyl, C(O)NHOH,

N(CH$_3$)$_2$, C(O)CH$_3$, C(O)—N(CH$_3$)OH, SO$_3$H, SCH$_3$, CHO, COOH, S(O)CH$_3$, SO$_2$CH$_3$, SO$_2$NH$_2$, SO$_2$NHCH$_3$, CN, CSNH$_2$, CH=N—OH, CONH$_2$, CONH(CH$_3$).

Representative examples of preferred

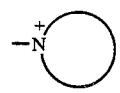

pyridinium groups are those having the formulae

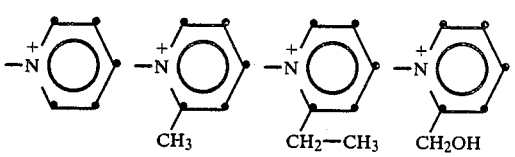

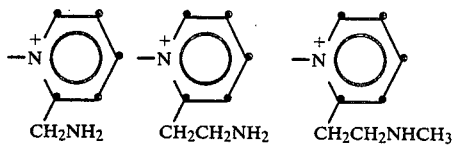

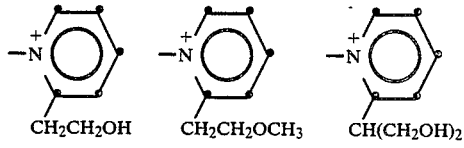

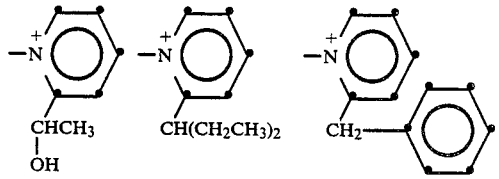

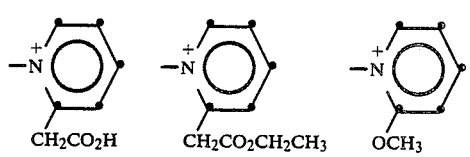

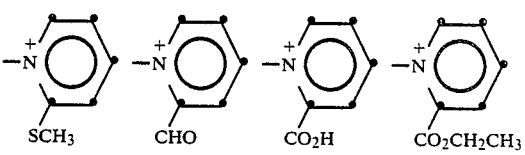

-continued
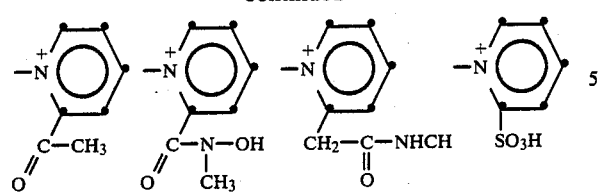
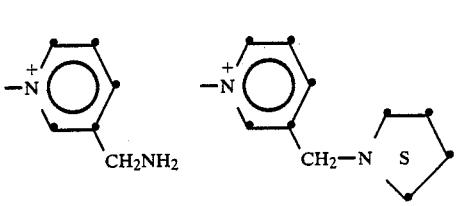
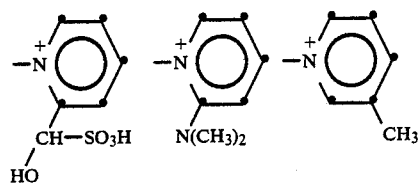
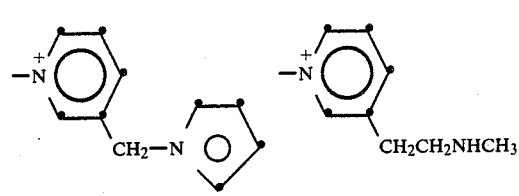
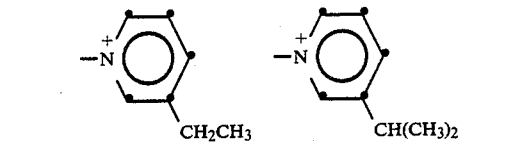
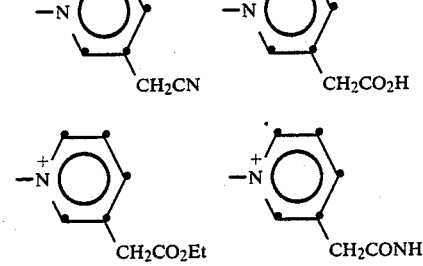
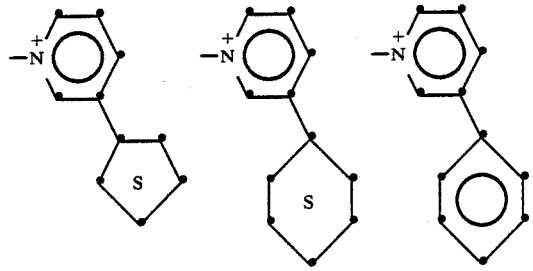
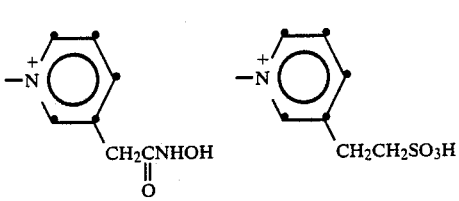
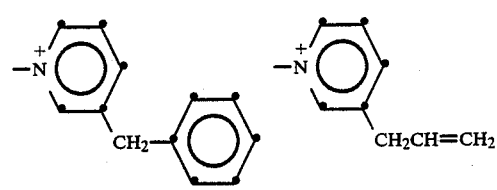
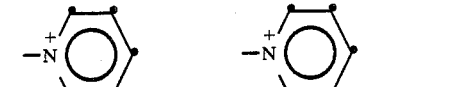
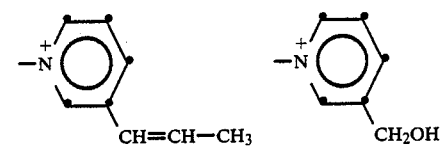
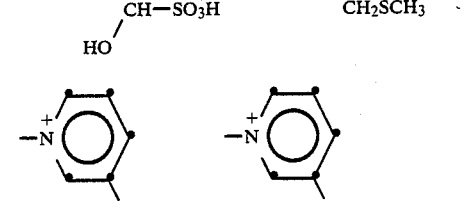
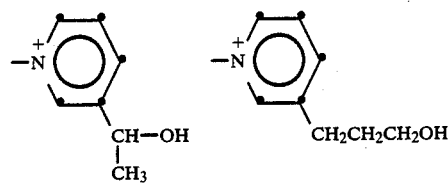
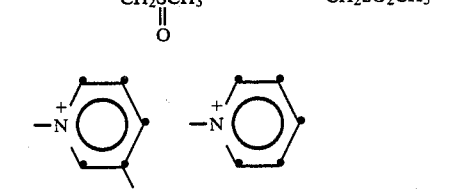
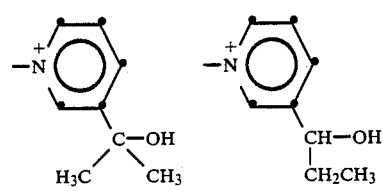

-continued
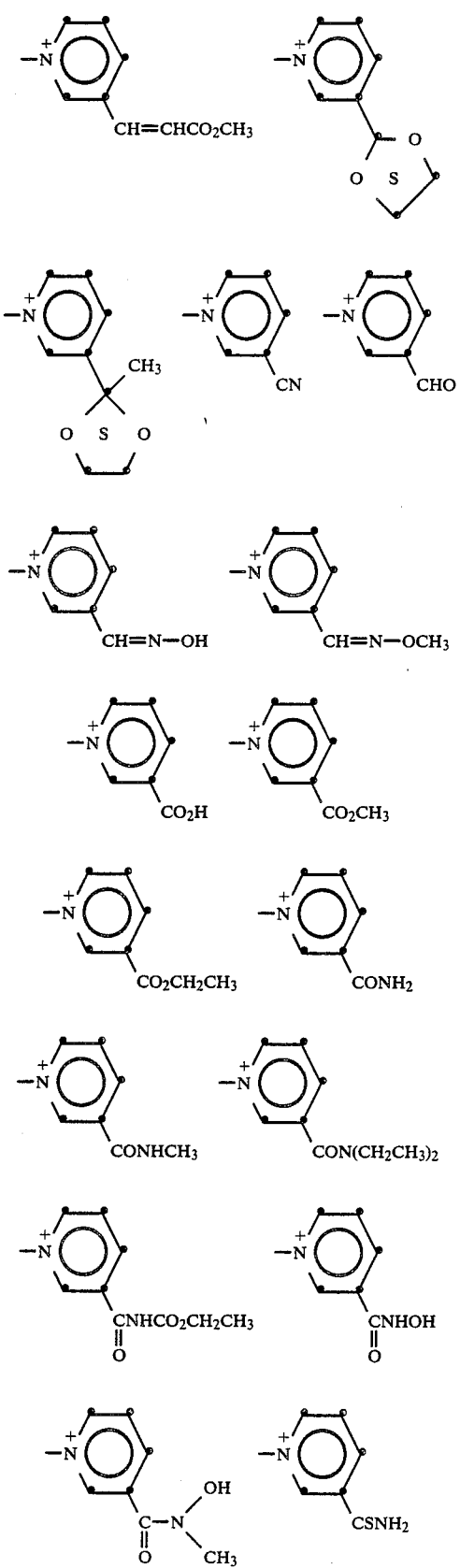
-continued
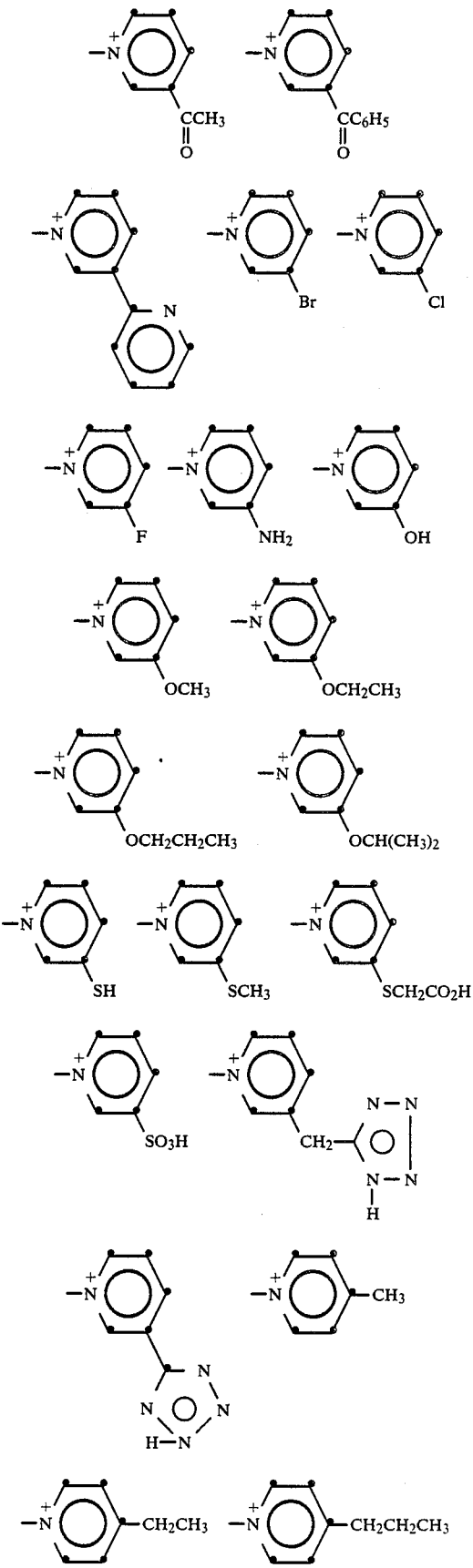

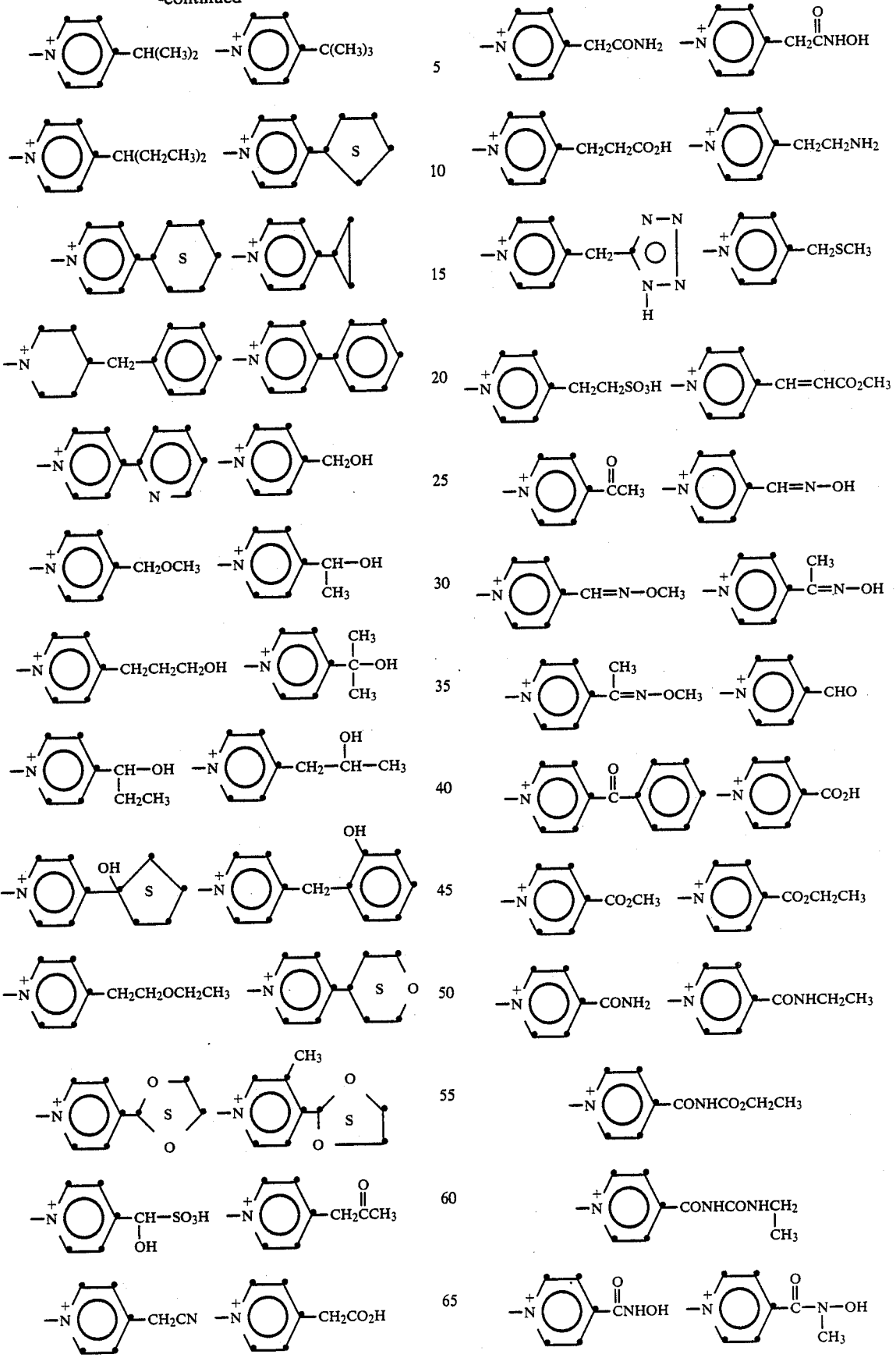

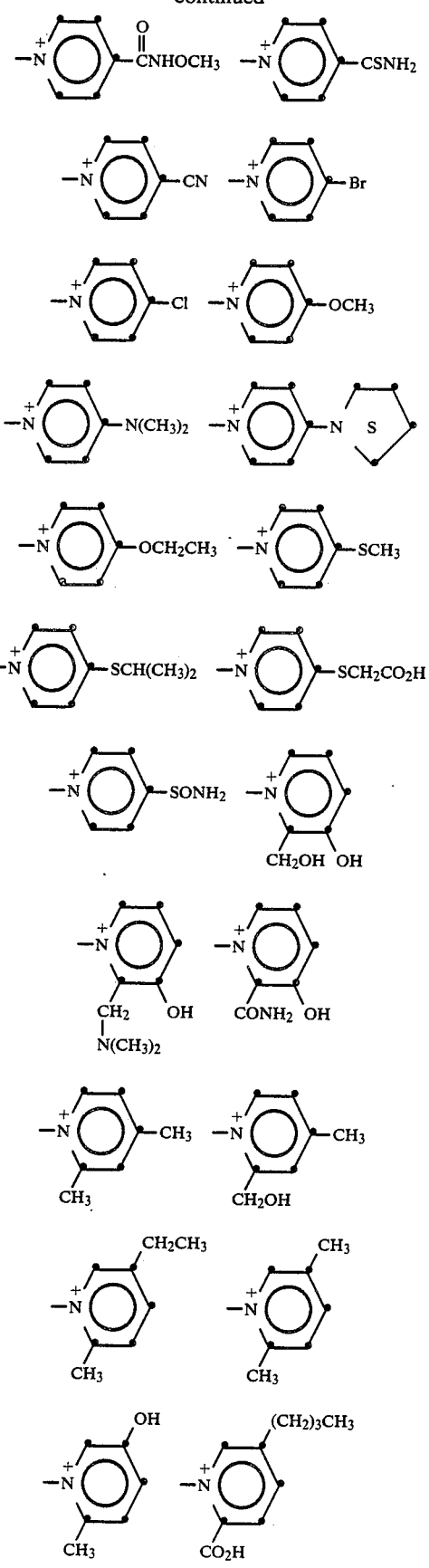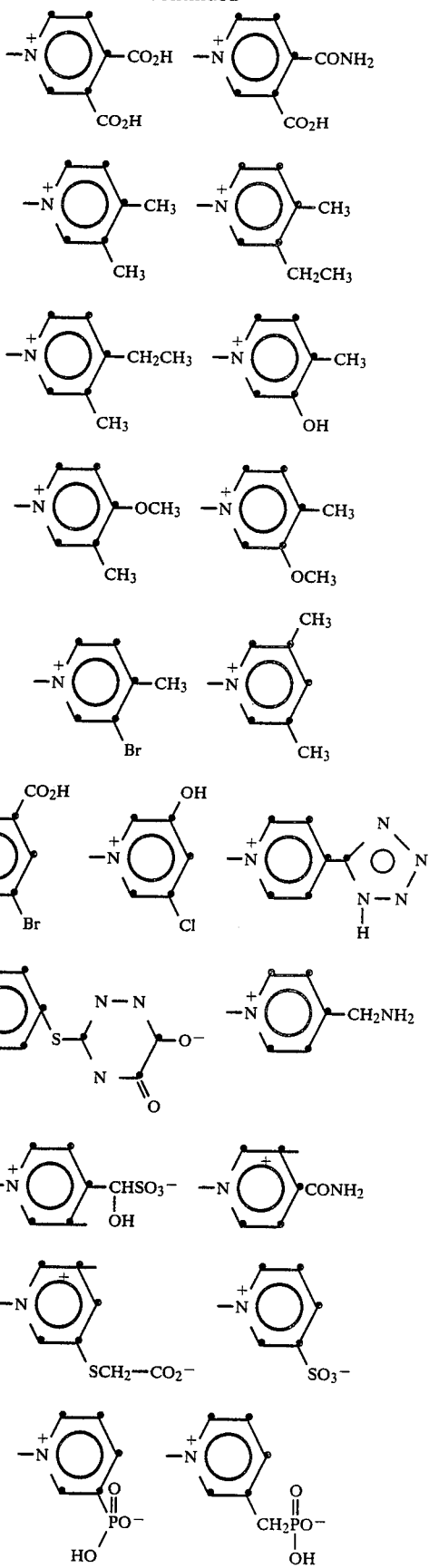

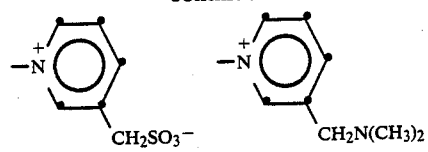

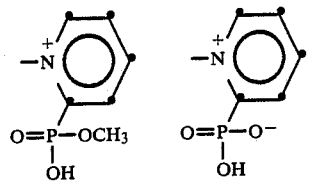

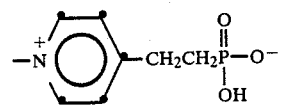

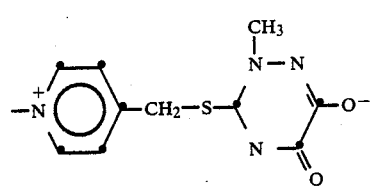

Representative examples of preferred monocyclic

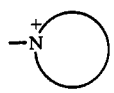

other then pyridinium are those having the following formulae:

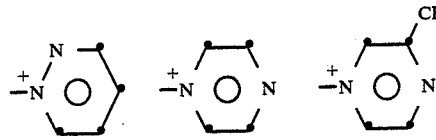

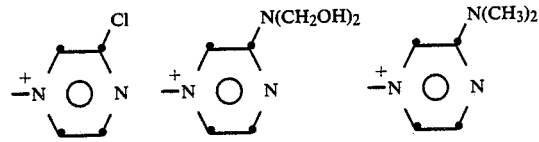

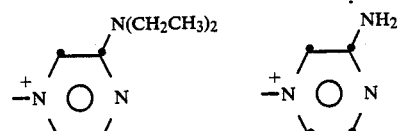

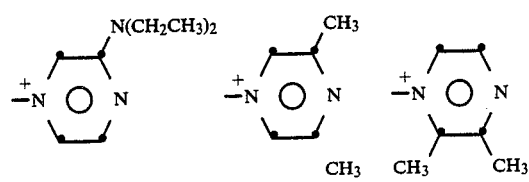

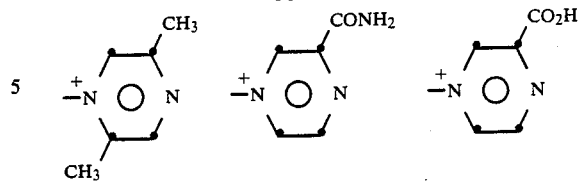

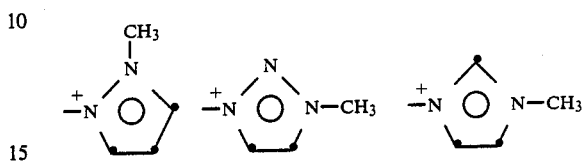

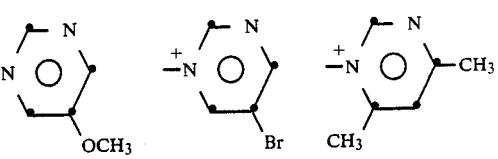

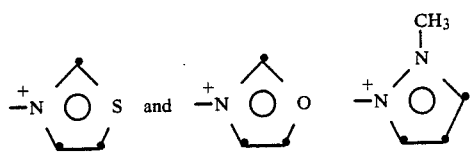

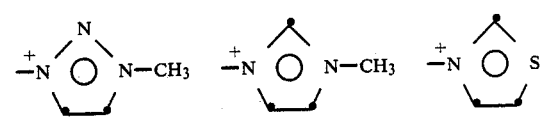

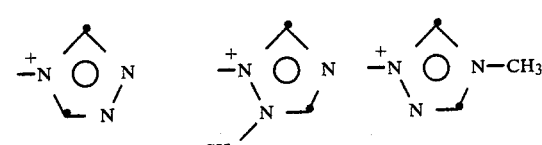

In another preferred embodiment, the —N+ group is a quaternized, bicyclic, substituted or unsubstituted heteroaryl, containing in addition to the quaternary N, up to 4 additional heteroatoms independently selected from O, N and S, and 9–10 total ring atoms.

Representative useful

groups are substituted and unsubstituted quinolinium, isoquinolinium, quinoxalinium, isocinolinium, thienopyridinium, furopyridinium, naphthyridinium, pyrazinopyridinium,

 D where D is a C$_{2-6}$ alkylene ring which may be interrupted by one or more O, S or N heteroatoms.

Preferred Formula I compounds are those where

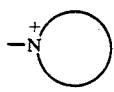

is a bicyclic 9 or 10 membered ring, and more preferably substituted or unsubstituted quinolinium, isoquinolinium, or thienopyridinium.

The preferred substituents on the bicyclic heteroaryl groups are OH, C$_1$–C$_3$alkyl, NH$_2$, CH=NOCH$_3$, CF$_3$, halo, preferably Br or Cl, O—C$_1$–C$_3$alkyl, COOH, CHO, SO$_3$H, CONH$_2$, SO$_2$NH$_2$, N(C$_1$–C$_3$alkyl)$_2$, CH$_2$CO$_2$H, CH$_2$OH,

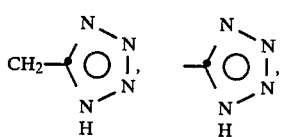

CH$_2$SO$_3$H, CN, CONH$_2$, CH$_2$CN, CH$_2$CONH$_2$, CH$_2$N(C$_1$–C$_3$alkyl)$_2$ and the like.

Representative examples of useful bicyclic

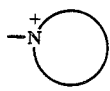

groups are:

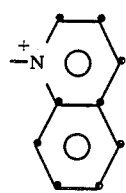  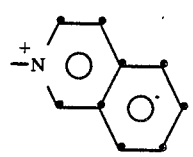  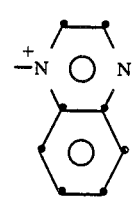

quinolinium    isoquinolinium    quinoxalinium

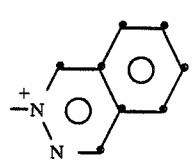  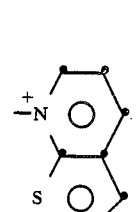  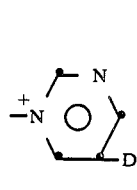

isocinolinium    thieno[2,3-b]pyridinium

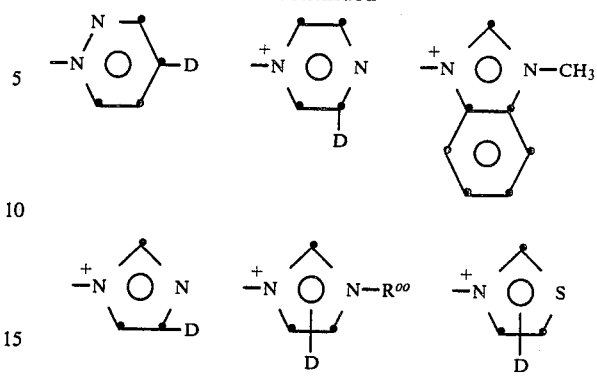

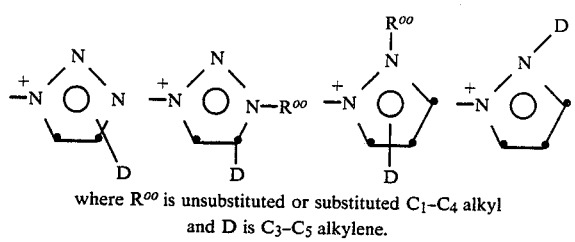

where R$^{oo}$ is unsubstituted or substituted C$_1$–C$_4$ alkyl and D is C$_3$–C$_5$ alkylene.

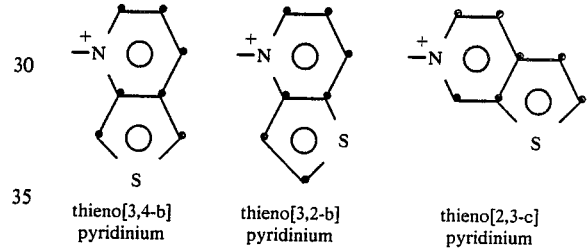

thieno[3,4-b] pyridinium    thieno[3,2-b] pyridinium    thieno[2,3-c] pyridinium

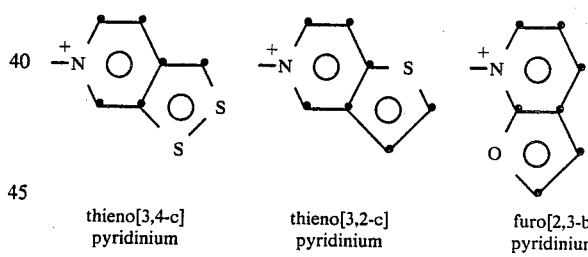

thieno[3,4-c] pyridinium    thieno[3,2-c] pyridinium    furo[2,3-b] pyridinium

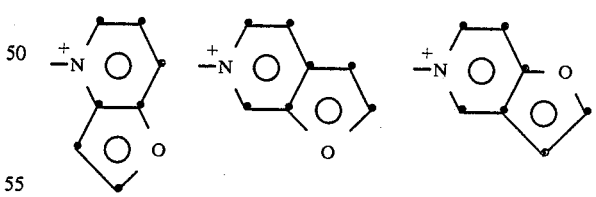

furo[3,2-b] pyridinium    furo[2,3-] pyridinium    furo[3,2-c] pyridinium

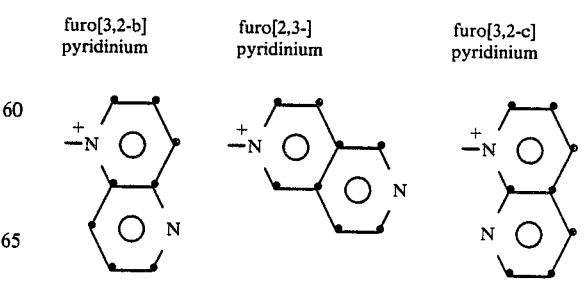

1,5-napthyridinium    1,7-napthyridinium    1,8-napthyridinium

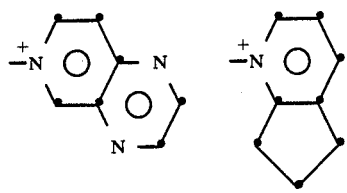
pyrazino[2,3-c]
pyridinium
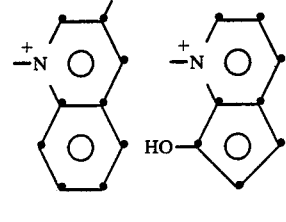
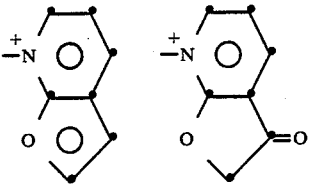
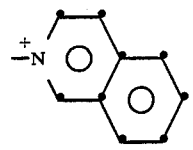
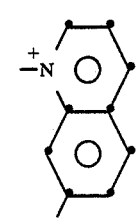
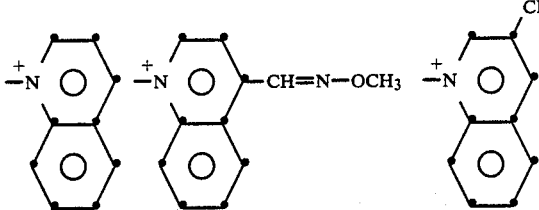
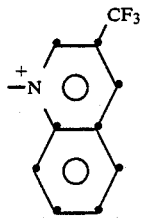
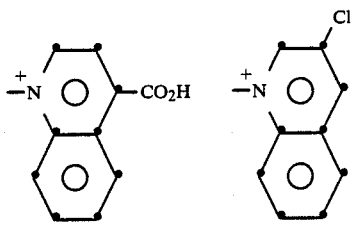
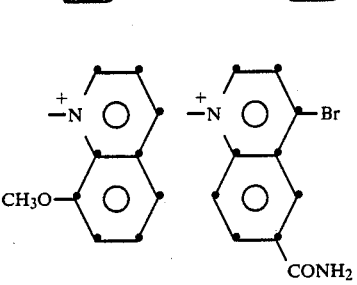

-continued
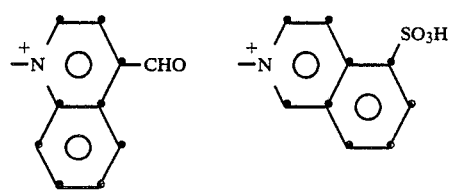
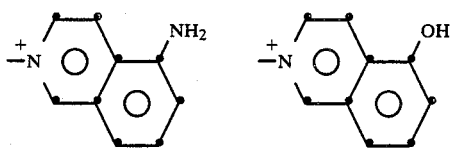
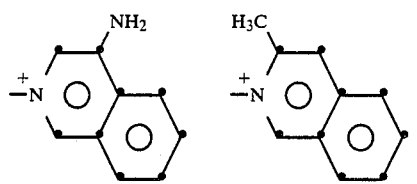
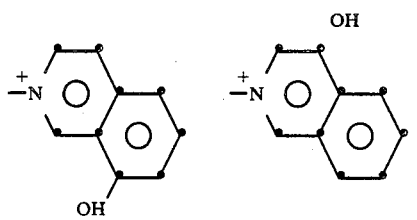
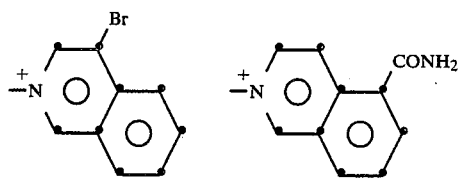
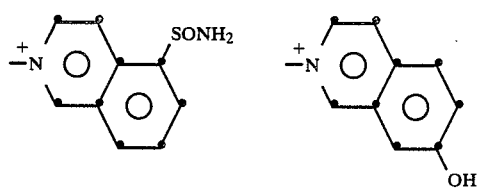
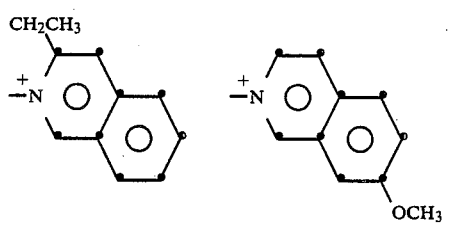
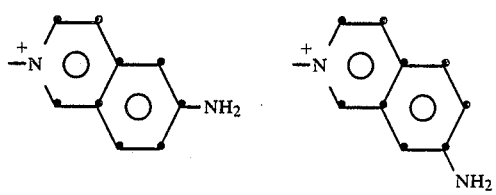
-continued
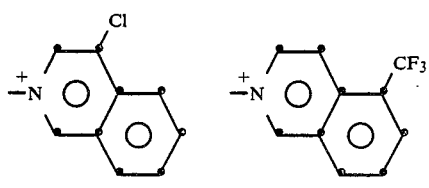
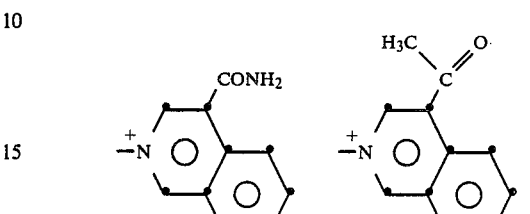
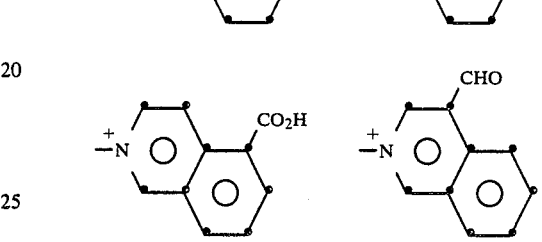
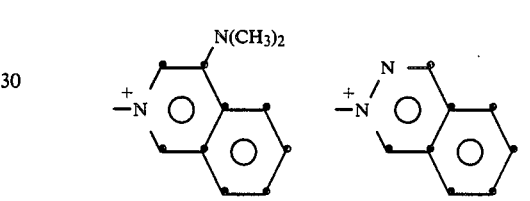
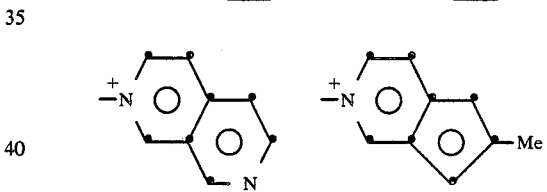
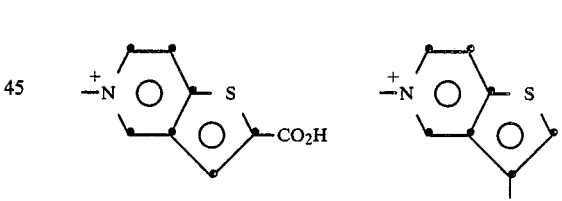
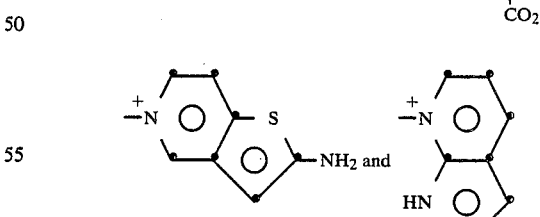
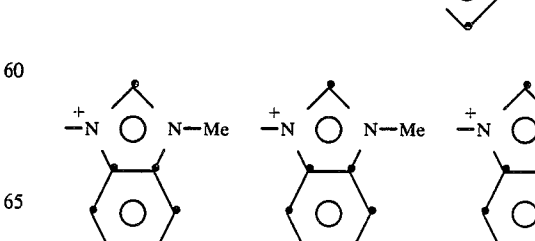

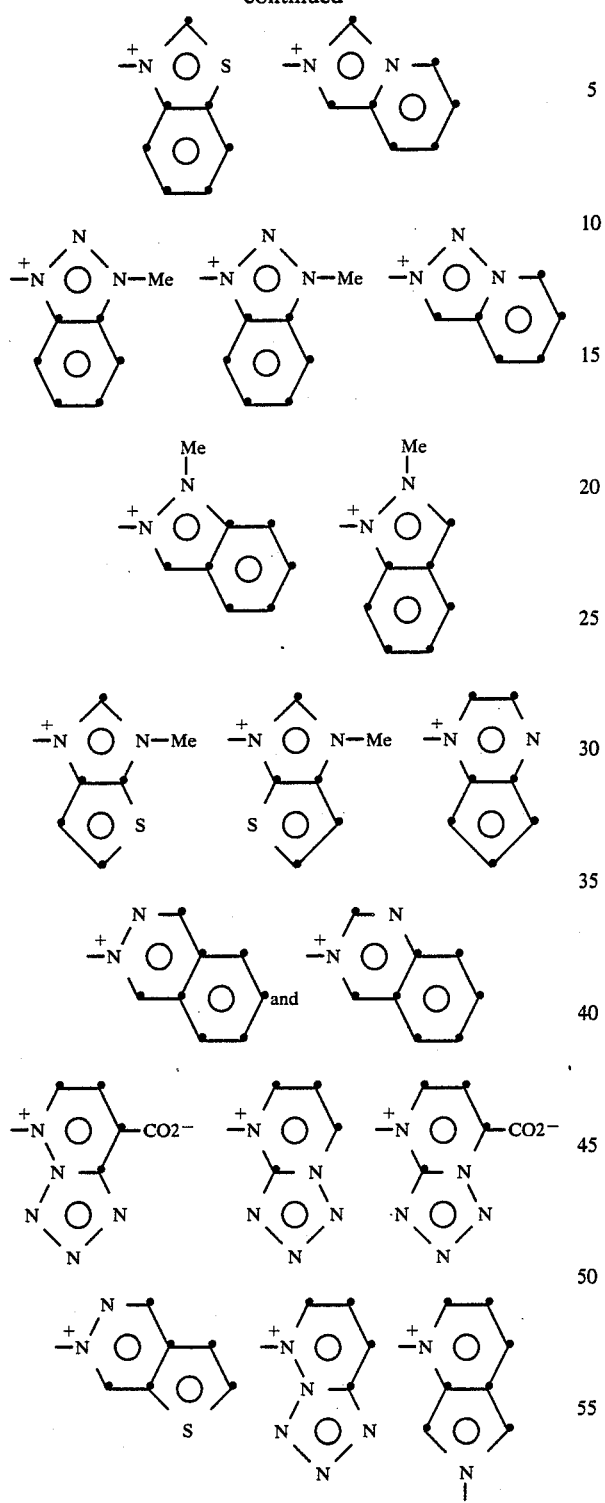
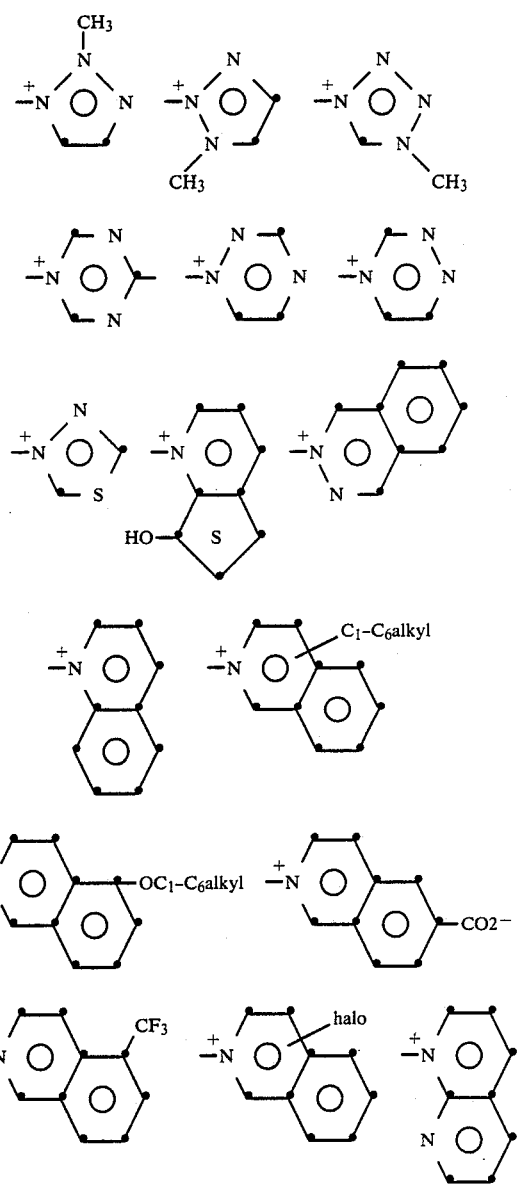
Where
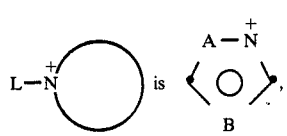
representative examples of preferred groups are:
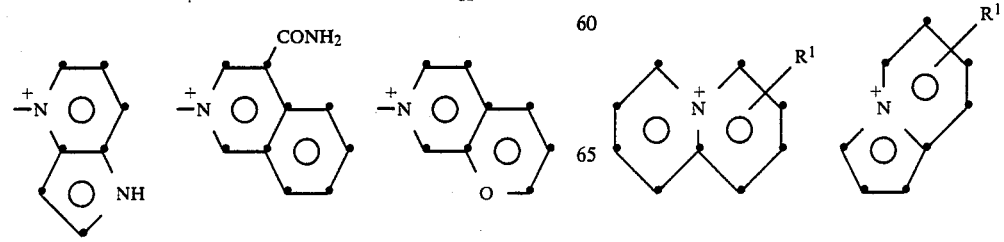

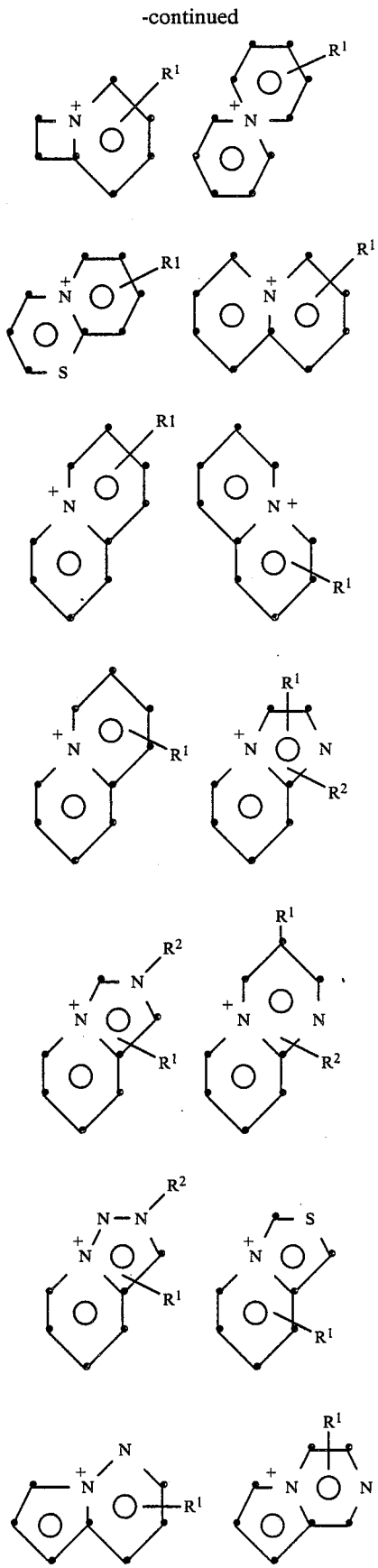

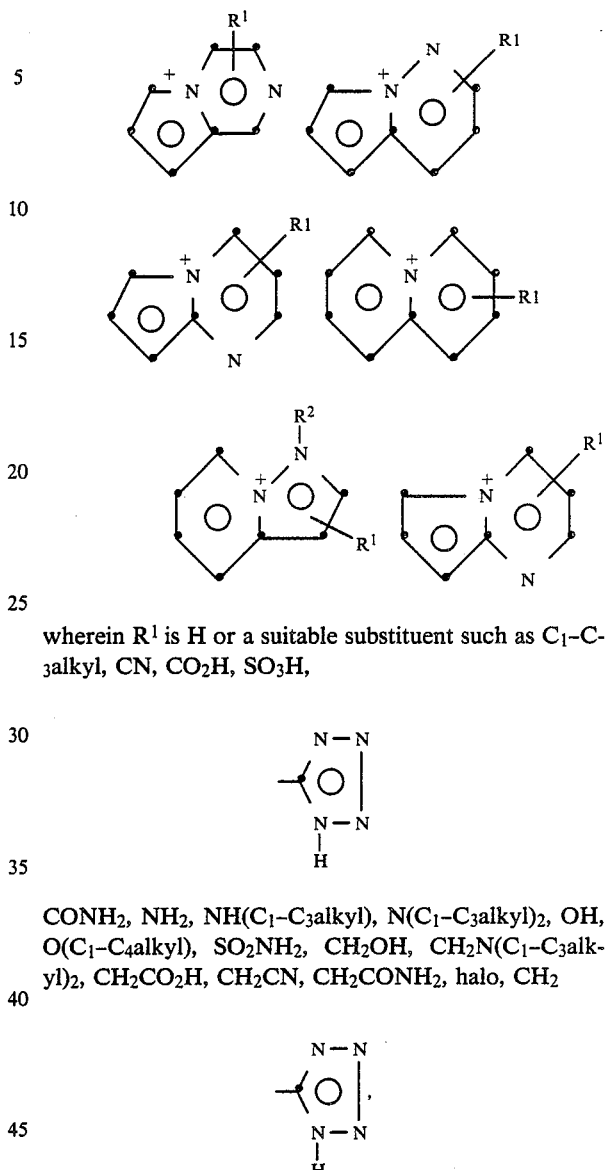

wherein $R^1$ is H or a suitable substituent such as $C_1$-$C_3$alkyl, CN, $CO_2H$, $SO_3H$,

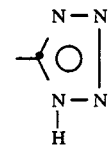

$CONH_2$, $NH_2$, $NH(C_1$-$C_3alkyl)$, $N(C_1$-$C_3alkyl)_2$, OH, $O(C_1$-$C_4alkyl)$, $SO_2NH_2$, $CH_2OH$, $CH_2N(C_1$-$C_3alkyl)_2$, $CH_2CO_2H$, $CH_2CN$, $CH_2CONH_2$, halo, $CH_2$

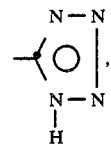

and $R^2$ substituted or unsubstituted $C_1$-$C_4$alkyl wherein the substituents are selected from OH, $N(C_1$-$C_3alkyl)_2$, $CO_2H$, $SO_3H$, CN, $CONH_2$, and $O(C_1$-$C_4alkyl)$.

Especially preferred

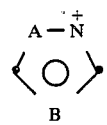

groups are the unsubstituted groups especially where (a) A is $(CH_2)_2$ or $(CH_2)_3$, and B is a single bond, (b) A is $CH_2$ and B is $CH_2$ or $(CH_2)_2$, or c) A is a single bond and B is $(CH_2)_{2-3}$, and the heteroaryl moiety is preferably pyridinium, thiazolium, or imidazolium.

The compounds of Formula I include inner (Zwitterion) salts when Y is $COO^-$ e.g.

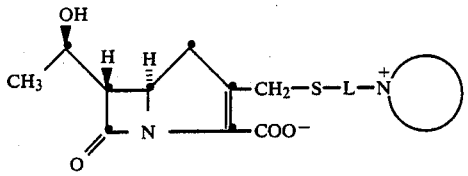

or, when Y is other than COO⁻, salts with an external, physiologically acceptable counterion $Z^{(-)}$ e.g.

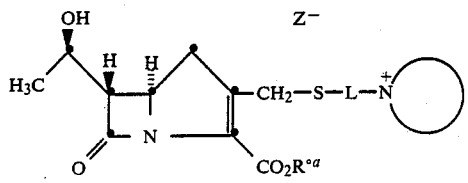

$R^{\circ a}$ is a pharmaceutically acceptable ester, e.g., pivaloyloxymethyl, phthalidyl, phthalimidomethyl, acetoxymethyl, ethoxycarbonyloxyethyl, pivaloyloxyethyl, 4-methyl-2-oxo-1,3-dioxolen-5-yl-methyl or salt group; and $Z^-$ is $Cl^-$, $Br^-$, $I^-$, $OH^-$, $HCO_3^-$, $CH_3CO_2^-$ and the like. The inner salts are preferred.

Again, the compounds of Formula I include the stereoisomers as mixtures and as separate isomers.

Compounds having the (5R,6S,8R) stereochemistry shown below are preferred

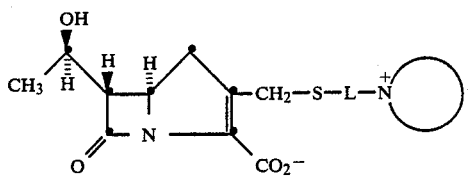

Where

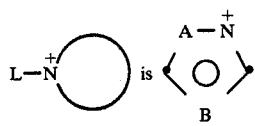

or when L contains a chiral center, the side chain chirality leads to diastereomeric products. The products can be separated by conventional methods, used as mixtures or synthesized stereospecifically from optically active mercaptans.

The compounds of the present invention (I) are valuable antibiotics active against various Gram-positive and Gram-negative bacteria and accordingly find utility in human and veterinary medicine. Representative pathogens which are sensitive to antibiotics I include: *Staphylococcus aureus, Escherichia coli, Klebsiella Pneumoniae, Bacillus subtilis, Salmonella typhosa, Pseudomonas* and *Bacterium proteus*. The antibacterials of the invention are not limited to utility as medicaments; they may be used in all manner of industry, for example: additives to animal feed, preservation of food, disinfectants, and in other industrial systems where control of bacterial growth is desired. For example, they may be employed in aqueous compositions in concentrations ranging from 0.1 to 100 parts of antibiotic per million parts of solution in order to destroy or inhibit the growth of harmful bacteria on medical and dental equipment and as bactericides in industrial applications, for example in waterbased paints and in the white water of paper mills to inhibit the growth of harmful bacteria.

The compounds of this invention may be used in any of a variety of pharmaceutical preparations. They may be employed in capsule, powder form, in liquid solution, or in suspension. They may be administered by a variety of means; those of principal interest include: topically or parenterally by injection (intravenously or intramuscularly).

Compositions for injection, a preferred route of delivery, may be prepared in unit dosage form in ampules, or in multidose containers. The compositions may take such forms as suspensions, solutions, or emulsions in oily or aqueous vehicles, and may contain formulatory agents. Alternatively, the active ingredient may be in powder form for reconstitution, at the time of delivery, with a suitable vehicle, such as sterile water. Topical applications may be formulated in hydrophobic or hydrophilic bases as ointments, creams, lotions, paints, or powders.

The dosage to be administered depends to a large extent upon the condition and size of the subject being treated as well as the route and frequency of administration—the parenteral route by injection being preferred for generalized infections. Such matters, however, are left to the routine discretion of the therapist according to principles of treatment well known in the antibiotic art. In general, a daily dosage consists of from about 5 to about 600 mg of active ingredient per kg of body weight of the subject in one or more treatments per day. A preferred daily dosage for adult humans lies in the range of from about 10 to 240 mg of active ingredient per kg of body weight. Another factor influencing the precise dosage regimen, apart from the nature of the infection and peculiar identity of the individual being treated, is the molecular weight of the chosen species of this invention (I).

The compositions for human delivery per unit dosage, whether liquid or solid, may contain from 0.1% to 99% of active material, the preferred range being from about 10-60%. The composition will generally contain from about 15 mg to about 1500 mg of the active ingredient; however, in general, it is preferable to employ a dosage amount in the range of from about 250 mg to 1000 mg. In parenteral administration, the unit dosage is usually the pure compound I in sterile water solution or in the form of a soluble powder intended for solution.

The preferred method of administration of the formula I antibiotic is parenteral by i.v. infusion, i.v. bolus, or i.m. injection.

For adults, 5-50 mg of Formula I antibiotic per kg of body weight given 2, 3, or 4 times per day is preferred. Preferred dosage is 250 mg to 1000 mg of the Formula I antibiotic given two (b.i.d.) three (t.i.d.) or four (q.i.d.) times per day. More specifically, for mild infections, and particularly urinary tract infections, a dose of 250 mg t.i.d. or q.i.d. is recommended. For moderate infections against highly susceptible gram positive and gram negative organisms, a dose of 500 mg t.i.d. or q.i.d. is recommended. For severe, life-threatening infections against organisms at the upper limits of sensitivity to the antibiotic, a dose of 1000 mg t.i.d. or q.i.d. is recommended.

For children, a dose of 5-25 mg/kg of body weight given 2, 3, or 4 times per day is preferred; a dose of 10 mg/kg t.i.d. or q.i.d. is usually recommended.

Antibiotic compounds of Formula I are of the broad class known as carbapenems or 1-carbadethiapenems. Certain of these carbapenems are susceptible to attack by a renal enzyme known as dehydropeptidase (DHP). This attack or degradation may reduce the efficacy of the carbapenem antibiotic. Inhibitors of DHP and their use with carbapenem antibiotics are disclosed in the prior art [see published European Patent Application No. 79102616.4 filed July 24, 1979 (Pat. No. 10573); 79102615.6, filed July 24, 1979 (Application No. 15573); and No. 82107174.3, filed Aug. 9, 1980 (Application No. 72014)].

The present I compounds may, where DHP inhibition is desired or necessary, be combined or used with the appropriate DHP inhibitor as described in the aforesaid published applications. Thus, to the extent that the cited European patent applications (1.) define the procedure for determining DHP susceptibility of the present carbapenems and (2.) disclose suitable inhibitors, combination compositions and methods of treatment, they are incorporated herein by reference. A preferred weight ratio of I compound:DHP inhibitor in the combination compositions is about 1:1. A preferred DHP inhibitor is 7-(L-2-amino-2-carboxyethylthio)-2-(2,2-dimethylcyclopropanecarboxamide)-2-heptenoic acid or a useful salt thereof.

These combination compositions and their use is another embodiment of the present invention.

The compounds of Formula I may be prepared by any convenient process.

PREPARATION OF COMPOUNDS OF FORMULA I

Due to the varied nature of Het, several different synthetic approaches are used to prepare compounds of type I. These are summarized below. Implicit in these synthetic routes is the fact that when Het contains a functional group which might interfere with the intended course of the reaction, the offending group is blocked. For example, when a basic nitrogen group is present as —NHR or —NH$_2$, it is usually protected by acylation (—CO$_2$-allyl or —CO$_2$PNB) or silylation. In the case of a carboxyl group, protection is achieved via use of a suitable ester, such as allyl or PNB.

In many instances, the actual order of carrying out the individual synthetic transformations in a synthetic scheme can be permuted for reasons of synthetic expediency. Thus, many of the examples listed below could proceed with equal facility by having the order of operations changed.

SYNTHETIC METHODOLOGY

A. Key Intermediate II

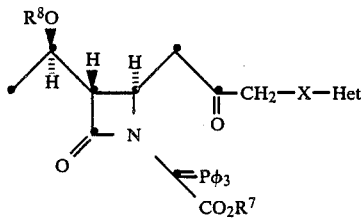

II

X and Het are as defined above;

R$^7$ is a suitable ester protecting group such as p-nitrobenzyl, allyl, or the like;

R$^8$ is a suitable alcohol protecting group such as (CH$_3$)$_3$Si—, t-BuMe$_2$Si, p-nitrobenzyloxycarbonyl, allyloxycarbonyl, or the like.

Method IIa

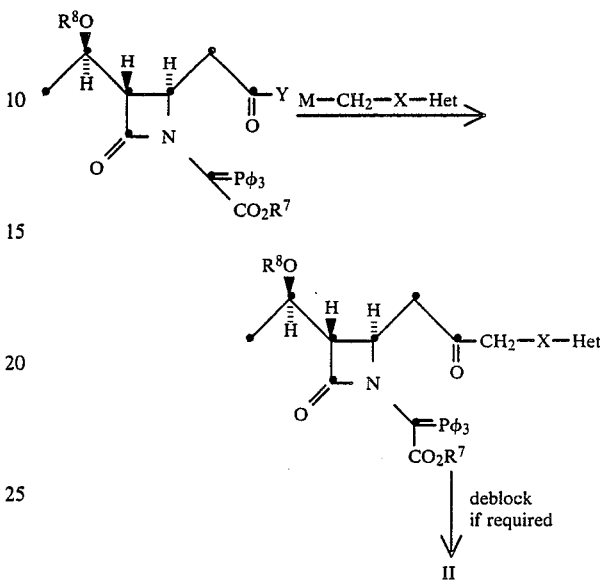

Y=

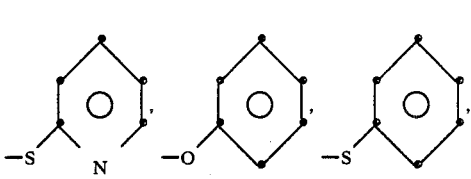

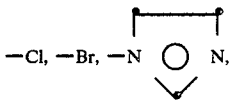

or the like;

R$^7$, and R$^8$ are as defined above;

M=Li, MgX, Cu or the like.

Method IIb

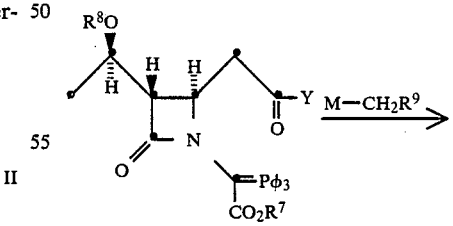

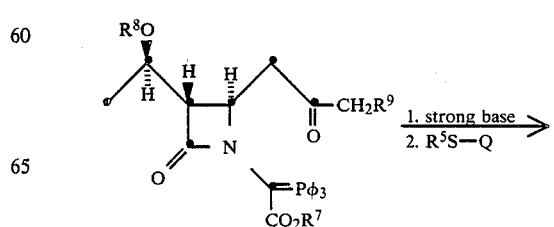

-continued

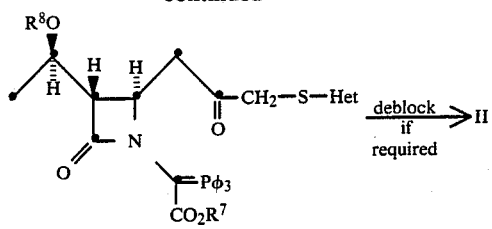

Y and M are as defined above;
R$^8$=triorganosilyl, allyloxycarbonyl, or the like;
R$^7$=allyl, benzyl or the like;
Q=—Cl, —Br, —SR, —SO$_2$R or the like;
R$^9$=H, CH$_3$;
strong base=LiNiPr$_2$, LiN(TMS)$_2$,

etc.

Method IId

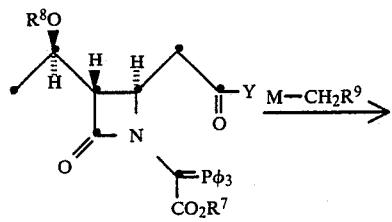

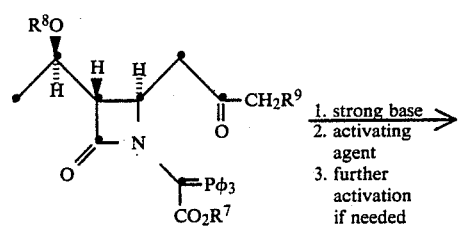

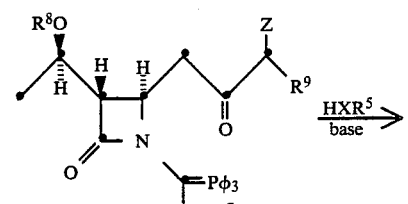

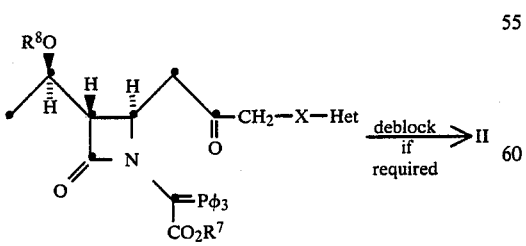

X, M, and Y are as defined above;
R$^7$=allyl, benzyl or the like;
R$^8$=triorganosilyl, allyloxycarbonyl, or the like;
strong base is as defined previously;

R$^9$=H, CH$_3$;
Z=OSO$_2$CH$_3$,

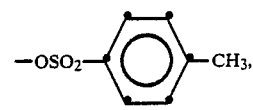

—Cl, Br, I or the like;
activating agent=O$_2$, MoOPH, Br$_2$, I$_2$, BrSO$_2$Ar etc.
The —OH product of reaction with O$_2$ or MoOPH can be further activated with ClSO$_2$CH$_3$,

 etc.

Method IIe

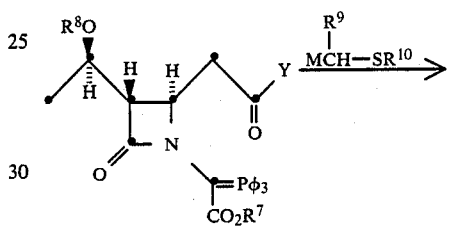

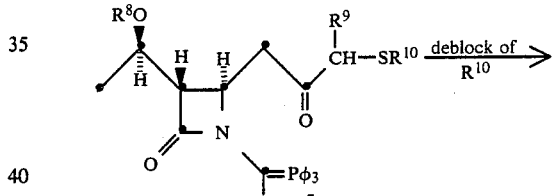

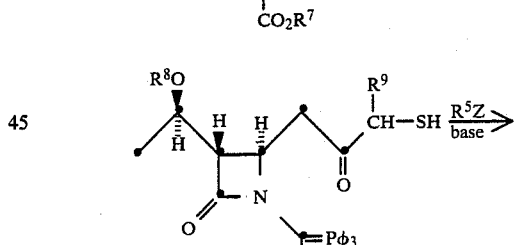

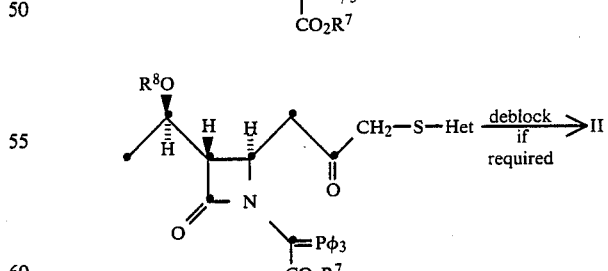

Z, R$^5$, M and Y are as defined previously;
R$^7$=allyl, benzyl or the like;
R$^8$=triorganosilyl, allyloxycarbonyl or the like;
R$^{10}$=—C$\phi_3$, -tetrahydropyranyl or the like;
R$^9$=H, CH$_3$;
in addition, Z can be an activated olefin or alkyne

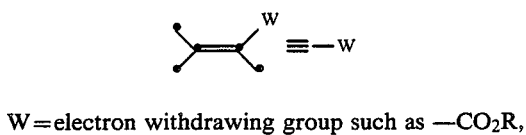
W = electron withdrawing group such as —CO$_2$R,
—CR,
 ‖
 O
—CN, —SO$_2$R, etc.
Variations of the above methodologies involving permutation of steps is also possible. For example, the phosphorane group on nitrogen can be introduced at a later stage by "standard" procedures (see below).
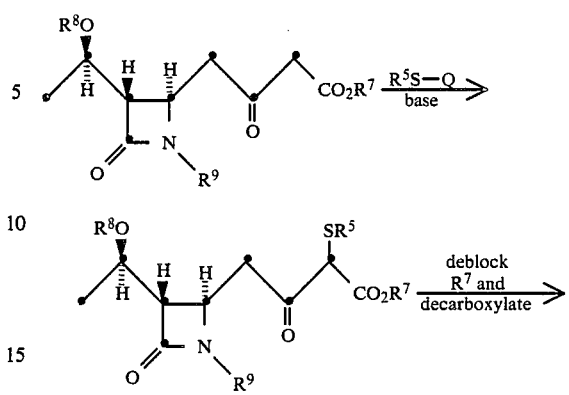
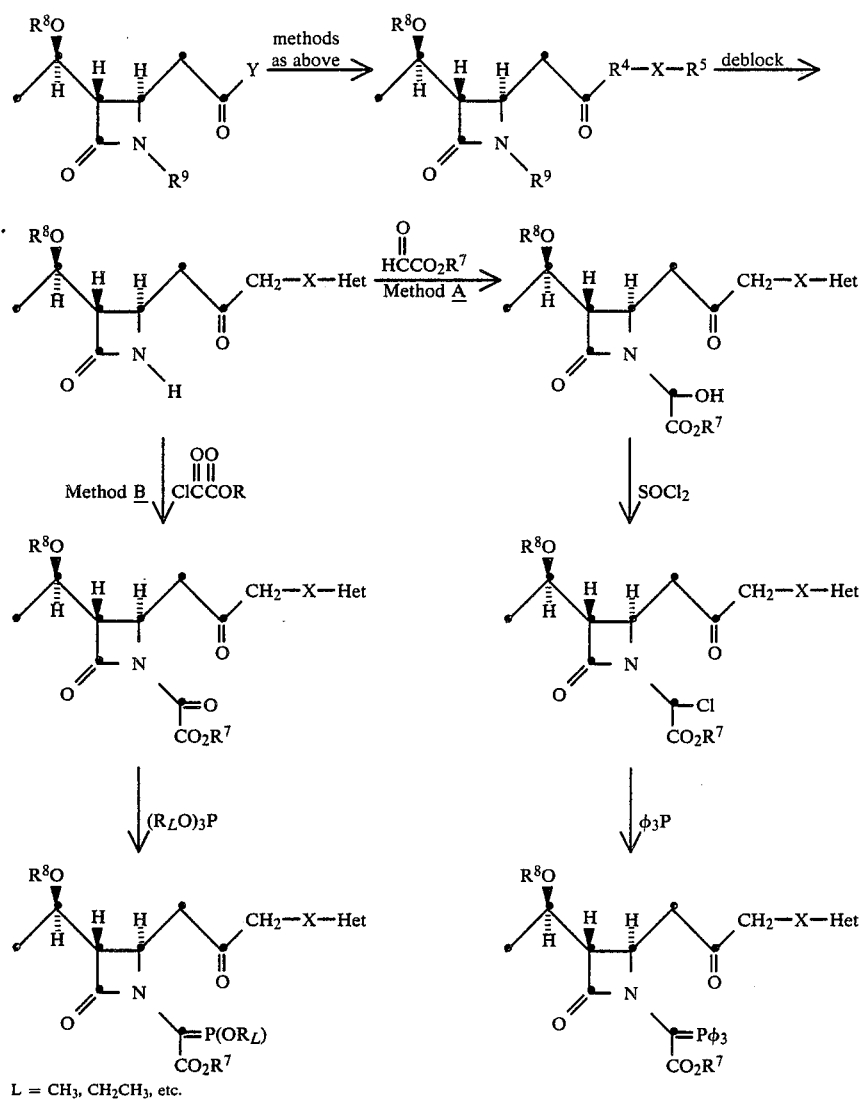
L = CH$_3$, CH$_2$CH$_3$, etc.
One example of such a route is shown in Method IIf.
Method IIf
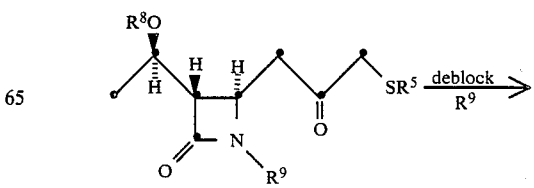

-continued
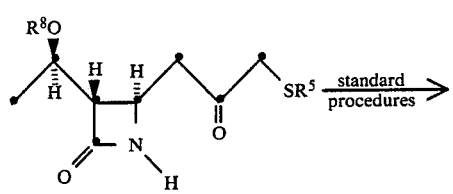
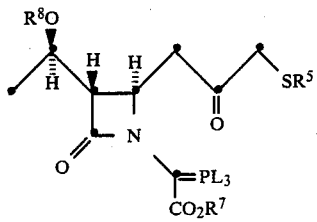
L = φ, OEt, etc.
Method IIg
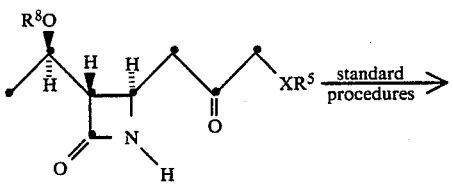
Y, $R^8$, $R^9$ are as previously defined;
R″=t-Bu, $R_3$Si such as $Me_3Si$, t-BuMe$_2$Si;
L=
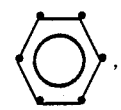
—OR such as OEt, OMe, OiPr, etc.
Method IIh
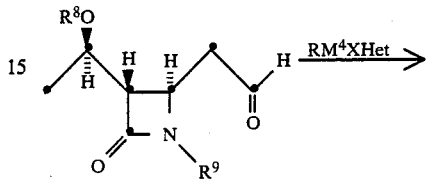
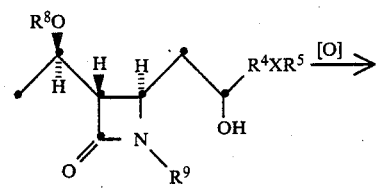
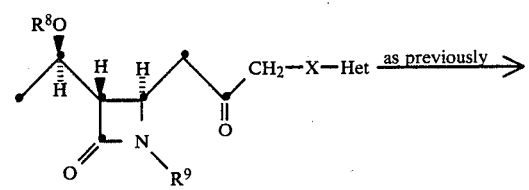
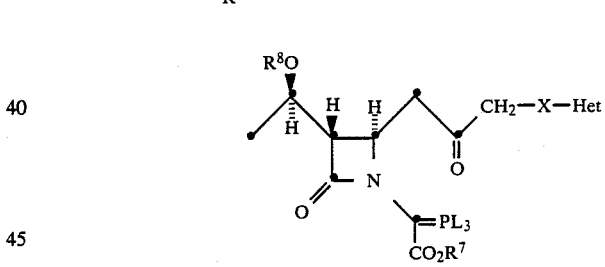
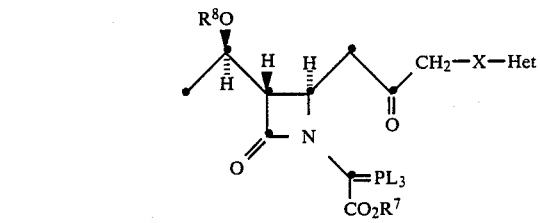
all substituents as previously defined
Method IIi
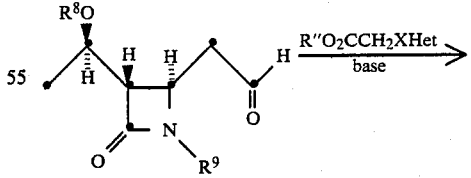
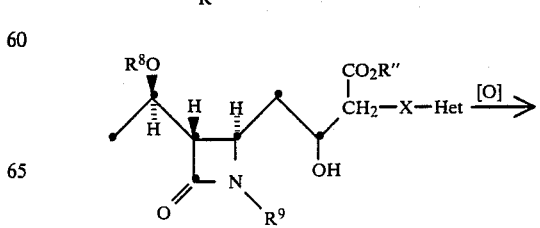

-continued

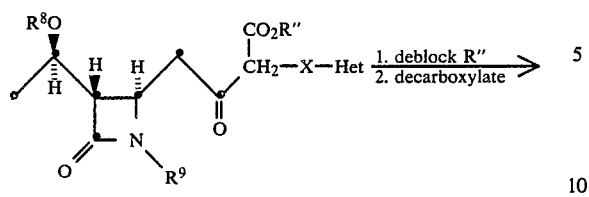

1. deblock R″
2. decarboxylate

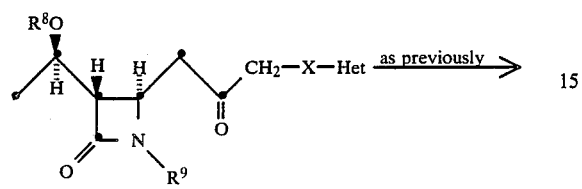

as previously

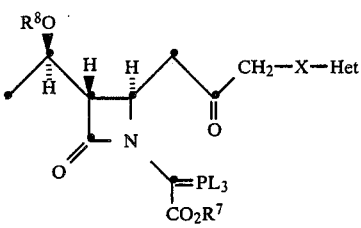

Completion of the Synthesis from Intermediate II—Methods a-i

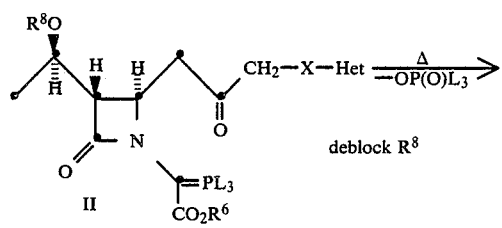

deblock $R^8$

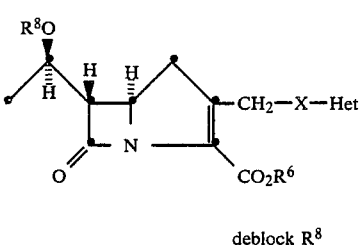

deblock $R^8$

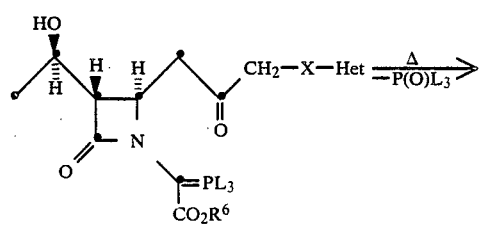

-continued

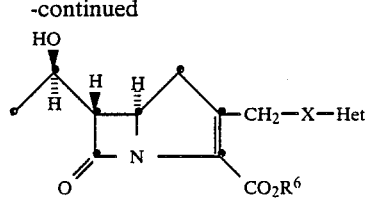

1. deblock side chain protecting group if necessary $\gamma$
2. deblock $R^6$

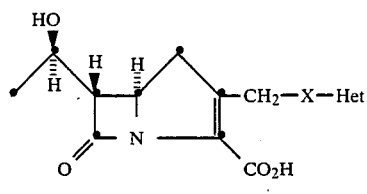

In those cases where the final product will contain a quaternized heterocyclic group, an additional alkylation step would be added.

Method j

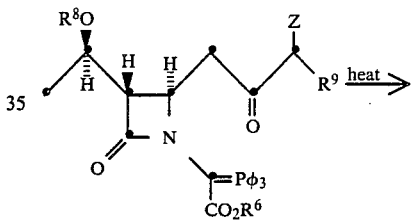

(prepared according to Method d)

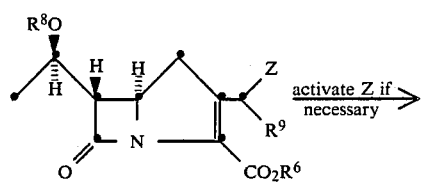

activate Z if necessary

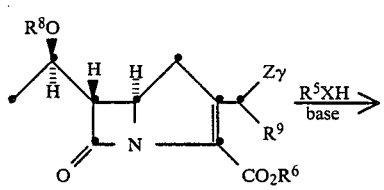

$R^5XH$ / base

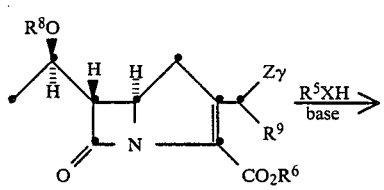

1. deblock side chain protecting
2. Alkylate N to form quaternary salt.
3. deblock $R^6$ -continued

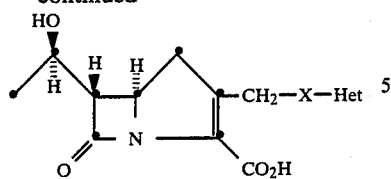

EXAMPLE 3

Utilizing the procedures of Examples 1–2, the following externally alkylated compounds listed in Table I are prepared, wherein $R^1$ for each compound is hydrogen. Remarks relative to the procedures are presented in the footnotes to Table I.

TABLE I

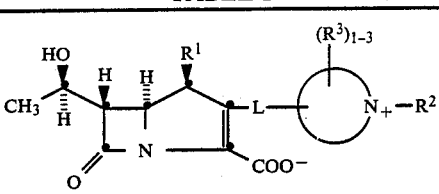

| Compound | L | ⟨N⟩ | $R^2$ |
|---|---|---|---|
| 1. | $CH_2$ | (4-pyridyl) | $CH_3$ |
| 2. | $CH\,CH_3$ | " | " |
| 3. | $CH_2CH_2$ | " | " |
| 4. | $CH_2CH_2CH_2$ | " | " |
| 5. | $CH_2CH_2$ | " | $CH_2CH_3$ |
| 6. | " | " | $CH_2CO_2H$ |
| 7. | " | " | $CH_2CONH_2$ |
| 8. | " | " | $CH_2$-(tetrazolyl) |
| 9. | " | " | $CH_2SOCH_3$ |
| 10. | " | (3-methyl-pyridinium) | $CH_3$ |
| 11. | $CH_2CH_2$ | (2,6-dimethylpyridinium) | $CH_3$ |

TABLE I-continued

| Compound | L | ⟨N⟩ | $R^2$ |
|---|---|---|---|
| 12. | $CH\,CH_3$ | (3,5-dimethylpyridinium) | " |
| 13. | $CH\,CH_3$ (branched) | (3,5-dimethylpyridinium) | " |
| 14. | $CH_2$ | (pyridinium) | $CH_3$ |
| 15. | " | " | $CH_2CH_3$ |
| 16. | " | " | $CH_2CO_2H$ |
| 17. | " | " | $CH_2CONH_2$ |
| 18. | " | " | $CH_2$-(tetrazolyl) |
| 19. | " | " | $CH_2SOCH_3$ |
| 20. | $CH_2CH_2$ | " | $CH_3$ |
| 21. | " | " | $CH_2CO_2H$ |
| 22. | " | " | $CH_2CONH_2$ |
| 23. | $CH_2$ | (3-methylpyridinium) | $CH_2$-(tetrazolyl) |
| 24. | $CH\,CH_3$ | " | $CH_3$ |
| 25. | " | " | $CH_2CH_3$ |
| 26. | $CH_2CH_2CH_2$ | " | $CH_3$ |
| 27. | $CH_2$ | (2-methylpyridinium) | $CH_3$ |
| 28. | " | " | $CH_2CH_3$ |
| 29. | " | " | $CH_2CO_2H$ |
| 30. | " | " | $CH_2CONH_2$ |

TABLE I-continued

| Compound | L | ring | R² |
|---|---|---|---|
| 31. | " | " | CH₂-[1,2,3-triazol-N-H] |
| 32. | " | " | $CH_2SOCH_3$ |
| 33. | $CH_2CH_2$ | " | $CH_2CO_2H$ |
| 34. | " | " | $CH_2CONH_2$ |
| 35. | " | " | CH₂-[1,2,3-triazol-N-H] (oxadiazole variant) |
| 36. | $CH_2CH_2$ | pyridinium | $CH_2SOCH_3$ |
| 37. | CH(CH₃) | " | $CH_3$ |
| 38. | $CH_2CH_2CH_2$ | " | $CH_3$ |
| 39. | $CH_2$ | methylpyridinium | $CH_3$ |
| 40. | $CH_2$ | thiazolium | $CH_3$ |
| 41. | " | " | $CH_2CH_3$ |
| 42. | $CH_2CH_2$ | " | $CH_3$ |
| 43. | $CH_2$ | methylthiazolium | " |
| 44. | $CH_2CH_2$ | " | " |
| 45. | " | methylthiazolium | " |
| 46. | " | thiazolium isomer | " |
| 47. | " | isoxazolium | " |
| 48. | " | oxazolium | " |
| 49. | $CH_2CH_2$ | oxazolium | $CH_3$ |
| 50. | " | N-methylimidazolium | " |
| 51. | $CH_2CH_2$ | N-methylimidazolium | $CH_3$ |
| 52. | " | N-methyltriazolium | " |
| 53. | " | N-methyltriazolium | " |
| 54. | " | N-methyltetrazolium | " |

TABLE I-continued

| Compound | L | (ring) | R² |
|---|---|---|---|
| 55. | " | (imidazole ring, +N, N-CH₃) | " |
| 56. | " | (thiazole ring, +N, S) | " |
| 57. | CH₂CH₂ | (thiazole ring, N+, S) | CH₃ |
| 58. | " | (oxazole ring, N+, O) | " |
| 59. | CH₂CH₂ | (oxazole ring, +N, O) | CH₃ |
| 60. | " | (triazole ring, +N, N-CH₃) | " |
| 61. | " | (triazole ring, N, N, N+) | " |
| 62. | " | (triazole ring, +N, N-CH₃) | " |
| 63. | " | (pyrrole-type ring, N+) | " |
| 64. | " | (ring with N+) | " |
| 65. | " | (ring with S, N+) | " |
| 66. | CH₂CH₂ | (ring with S, N+) | CH₃ |
| 67. | " | (ring with O, N+) | " |
| 68. | " | (ring with S, N) | " |
| 69. | " | (ring with N+, S, N) | " |
| 70. | " | (ring with N+, S, N) | " |
| 71. | " | (naphthalene with +N) | " |
| 72. | " | (benzimidazole, N+, N-CH₃) | " |

TABLE I-continued

[Structure: bicyclic β-lactam with HO-CH(CH₃)-, H, H, R¹ substituents, L linker to ring with (R³)₁₋₃ and N⁺—R², COO⁻]

| Compound | L | ring (N) | R² |
|---|---|---|---|
| 73. | CH₂CH₂ | benzothiazolium | CH₃ |
| 74. | " | benzoxazolium | " |
| 75. | CH₂ | 2-methylthiazolium | CH₃ |
| 76. | " | thiazolium | " |
| 77. | " | oxazolium | " |
| 78. | " | isoxazolium | " |
| 79. | " | isoxazolium (O,N⁺) | " |
| 80. | " | N-methyl imidazolium | " |
| 81. | " | N-methyl imidazolium | " |
| 82. | " | N-methyl 1,2,3-triazolium | " |
| 83. | " | N-methyl 1,2,3-triazolium | " |
| 84. | CH₂ | N-methyl imidazolium | CH₃ |
| 85. | " | N-methyl imidazolium | " |
| 86. | CH₂ | thiazolium | CH₃ |
| 87. | " | thiazolium | " |
| 88. | " | isoxazolium | " |
| 89. | " | isoxazolium | " |
| 90. | " | N-methyl tetrazolium | " |

TABLE I-continued

Structure (left and right columns, same):

Compound 91–110 with L, ring, R² substituents.

| Compound | L | Ring | R² |
|---|---|---|---|
| 91. | " | 1,2,3-triazolium N-CH₃ ring | " |
| 92. | " | tetrazolium N-CH₃ ring | " |
| 93. | " | isoxazolium (N+−O) ring | " |
| 94. | CH₂ | isoxazolium ring | CH₃ |
| 95. | " | isothiazolium ring | " |
| 96. | " | isothiazolium ring (isomer) | " |
| 97. | CH₂ | oxazolium ring | CH₃ |
| 98. | " | thiazolium ring | " |
| 99. | " | thiadiazolium ring | " |
| 100. | " | quinolinium (fused bicyclic) | " |
| 101. | " | benzimidazolium N-CH₃ | " |
| 102. | CH₂ | benzothiazolium | CH₃ |
| 103. | " | benzoxazolium | " |
| 104. | " | pyridinium | CH₂CN |
| 105. | CH₂CH₂ | " | CH₂CN |
| 106. | CH₃CHCH₂ | " | CH₃ |
| 107. | " | pyridinium | " |
| 108. | CH₂ | pyridinium | CH₂CN |
| 109. | CH₂CH₂ | " | " |
| 110. | " | pyridinium | " |

TABLE I-continued
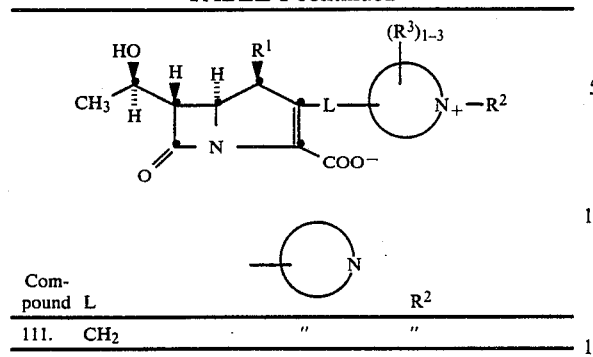
| Compound | L | ⟨N⟩ | R² |
|---|---|---|---|
| 111. | CH₂ | " | " |
Internally Alkylated Heteroaryliums—General Procedures
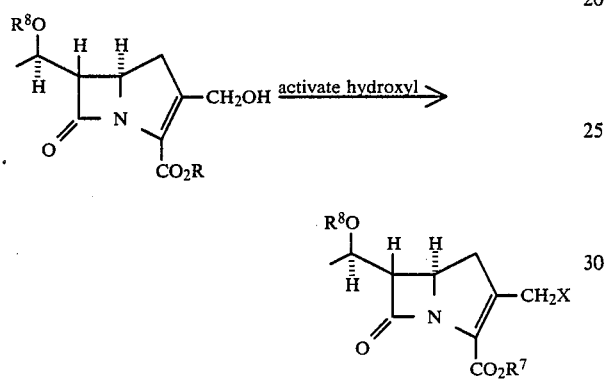
$X = Cl, Br, -OSO_2CH_3, -OSO_2-\text{C}_6\text{H}_4-CH_3$
$-O-\overset{\oplus}{P}\phi_3 Z^{\ominus}$
Method I
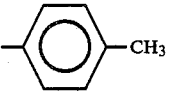
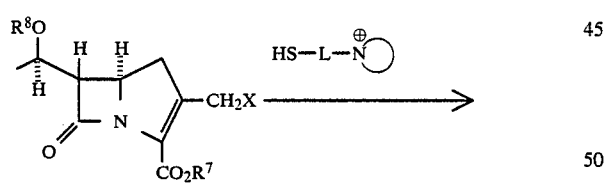
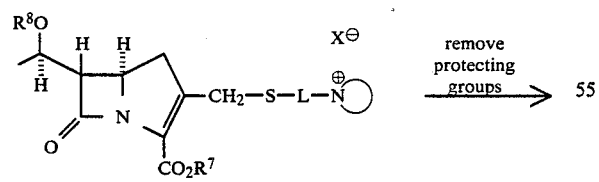
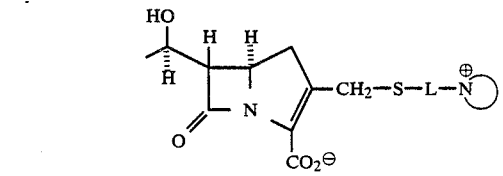
Method II
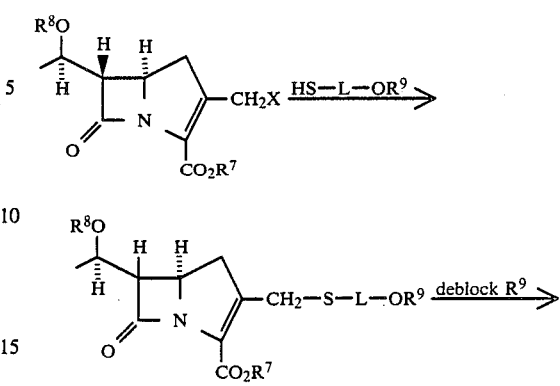
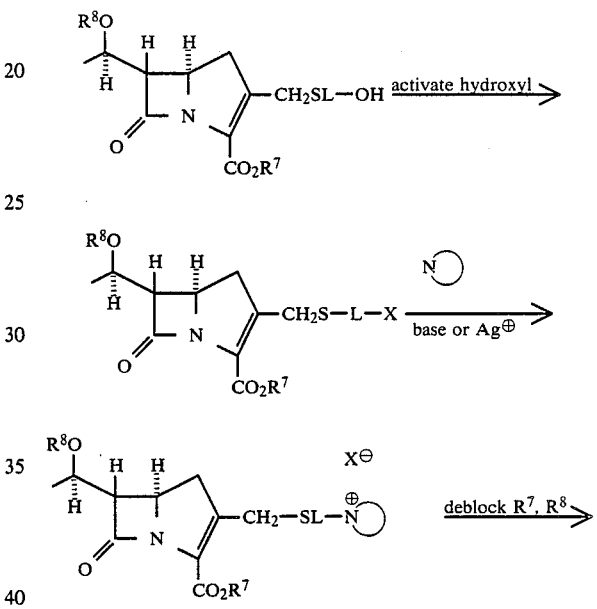
Method III
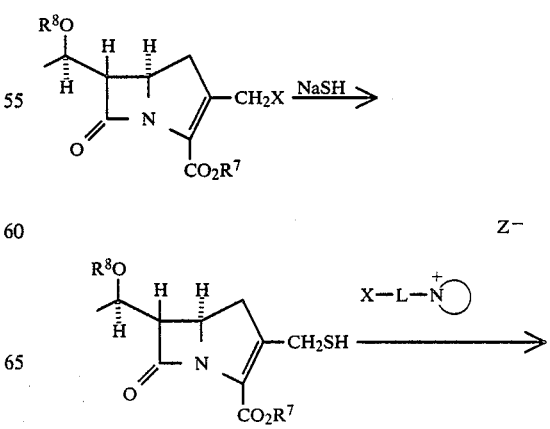

4,725,594
57
-continued
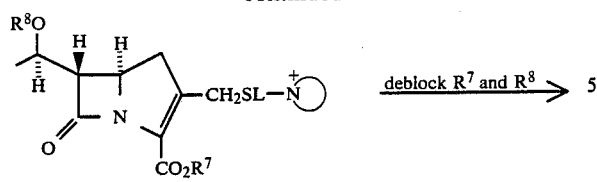
deblock R⁷ and R⁸ → 5
58
-continued
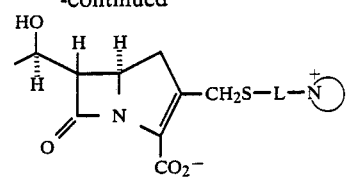
EXAMPLE 4
Preparation of:
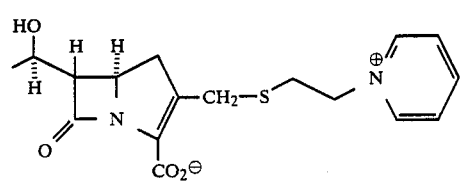
107
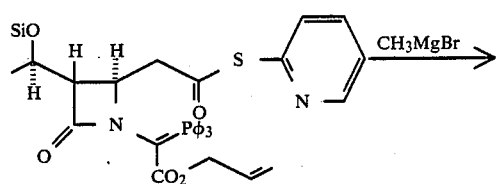 CH₃MgBr →
100
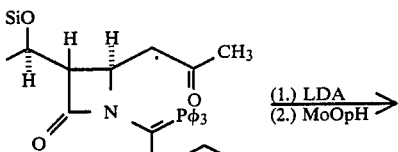 (1.) LDA (2.) MoOpH →
101
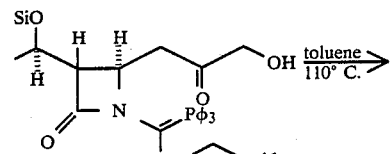 toluene 110° C. →
102
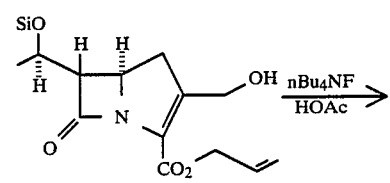 nBu₄NF HOAc →
103
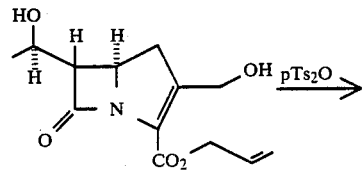 pTs₂O →
104

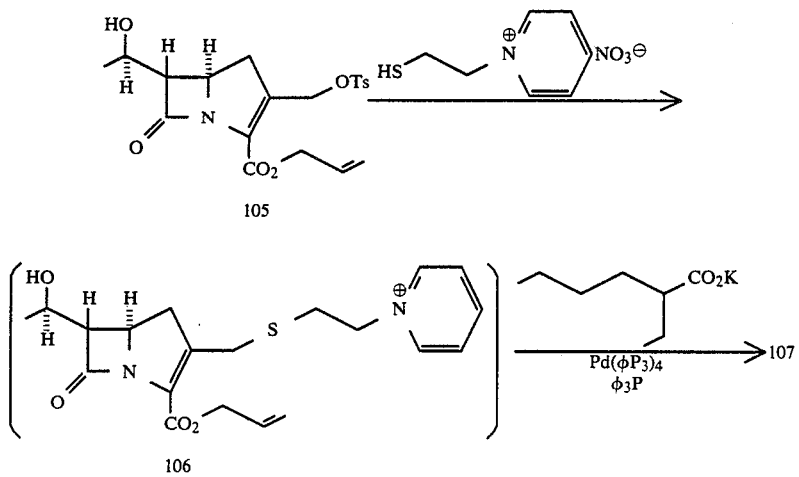

A commercial sample of 3M methyl magnesium bromide in ether (0.690 ml, 2.07 mmol) is added dropwise to a solution of pyridylthioester 100 (1.0 g, 1.4 mmol) in anhydrous tetrahydrofuran (25 ml) at −78° C. under dry nitrogen. After 10 min. an additional portion of methyl magnesium bromide (0.140 ml, 0.42 mmol) is added and stirring is continued for 20 min. The reaction mixture is then added to saturated ammonium chloride solution (35 ml), water (10 ml) and ethyl acetate (40 ml). The phases are separated and the aqueous layer is extracted with an additional portion of ethyl acetate (15 ml). The combined organic layers are washed with cold 1N hydrochloric acid solution, cold 10% aqueous sodium bicarbonate solution, water and brine. After drying over anhydrous magnesium sulfate the organic phase is concentrated in vacuo and the residual gum is chromatographed on silica gel (eluting with 0–10% ethyl acetate in methylene chloride) to yield methyl ketone 101.

To a solution of diisopropyl amine (0.120 ml, 0.87 mmol) in anhydrous tetrahydrofuran (9 ml) at 0° C. under nitrogen is added 1.3M n-butyl lithium in hexane (0.670 ml, 0.87 mmol). After 10 min. at 0° C. the solution is cooled to −78° C. and a solution of methyl ketone 101 (375 mg, 0.58 mmol) in anhydrous tetrahydrofuran (2 ml) is added by syringe. The resulting solution is stirred at −78° C. for 5 min. then oxodiperoxymolybdenum(pyridine)hexamethylphosphoramide (380 mg, 0.88 mmol) is added. The temperature is allowed to rise to −30° C. and the reaction is stirred for 30 min. The reaction is quenched by the addition of saturated sodium sulfite solution (6 ml), 1M potassium dihydrogen phosphate solution (2.4 ml), water (10 ml) and ethyl acetate (25 ml), followed by vigorous stirring for 15 min. After phase separation the aqueous layer is extracted with an additional portion of ethyl acetate (10 ml) and the combined organics are dried over anhydrous magnesium sulfate. Removal of the solvents in vacuo yields an oil which is chromatographed on silica gel (eluting with ethyl acetate/hexanes) to give hydroxy methyl ketone 102.

A solution of hydroxymethyl ketone 102 (330 mg, 0.50 mmol) in deoxygenated toluene (10 ml) is heated at reflux under an atmosphere of nitrogen for 1.5 hr., then is cooled and concentrated in vacuo. The resulting oil is chromatographed on silica gel prep plates (eluting with ethyl acetate/hexane) to provide hydroxymethyl carbapenem 103.

A solution of carbapenem 103 (95.3 mg, 0.25 mmol), glacial acetic acid (150 mg, 2.5 mmol), and 1M tetrabutyl ammonium fluoride in tetrahydrofuran (1.25 ml, 1.25 mmol) is stirred at ambient temperature for 30 hr. under a nitrogen atmosphere. The reaction mixture is then added to 0.5M pH 7 phosphate buffer (25 ml), water (25 ml), and ethyl acetate (50 ml). The layers are separated and the aqueous layer is extracted with an additional portion of ethyl acetate. The combined organic layers are washed with brine and dried over anhydrous magnesium sulfate. The dried solution is concentrated in vacuo and the residue is chromatographed on silica gel prep plates (eluting with ethyl acetate/hexane) to yield dihydroxycarbapenem 104.

A solution of dihydroxycarbapenem 104 (48 mg, 0.18 mmol) and p-toluene sulfonic anhydride (55 mg, 0.18 mmol) in anhydrous methylene chloride (5 ml) is cooled to 0° C. and triethylamine (20 mg, 0.20 mmol) is added slowly by syringe. The resulting solution is stirred at 0° C. for 1 hr, then is diluted with methylene chloride (20 ml) and washed quickly with cold pH 7 phosphate buffer and brine. The organic phase is dried over anhydrous sodium sulfate and the solvent is removed in vacuo to provide crude tosylate 105 which is carried on without further purification.

An ice cold solution of crude tosylate 105 (59 mg, 0.14 mmol) in anhydrous acetonitrile (5 ml) is treated with 1-(2-mercaptoethyl)pyridinium nitrate (34 mg, 0.17 mmol) and diisopropylethylamine (22 mg, 0.17 mmol). The resulting solution is stirred at 0° C. for 10 min., then added to a suspension of celite in diethyl ether (10 ml) and stirred briefly. The celite is filtered off and washed with an additional portion of ether, then is extracted with 1:1 tetrahydrofuran/water. The extract is concentrated in vacuo and lyophilized to give pyridinium salt 106. This material is suspended in a mixture of methylene chloride (2 ml) and ethyl acetate (2 ml). To this mixture is added a solution of potassium ethylhexanoate in ethyl acetate (0.360 ml of 0.5M solution, 0.18 mmol), triphenyl phosphine (3.3 mg, 0.013 mmol) and tetrakis(triphenylphosphine)palladium[0] (0.5 mg, 0.0005 mmol). The reaction mixture is stirred under nitrogen at ambient temperature for 2 hr., then is concentrated in vacuo. The residue is partitioned between water (5 ml) and ethyl ether (5 ml). The aqueous phase is separated and washed with an additional portion of ether, then is concentrated in vacuo and chromatographed on two RPS plates (eluting with ethanol/water). The U.V. active band is removed from the plates and extracted with 4:1 acetonitrile/water. This solution is washed four times with hexanes, then concentrated in vacuo and lyophilized to yield compound 107.

EXAMPLE 5

Preparation of:

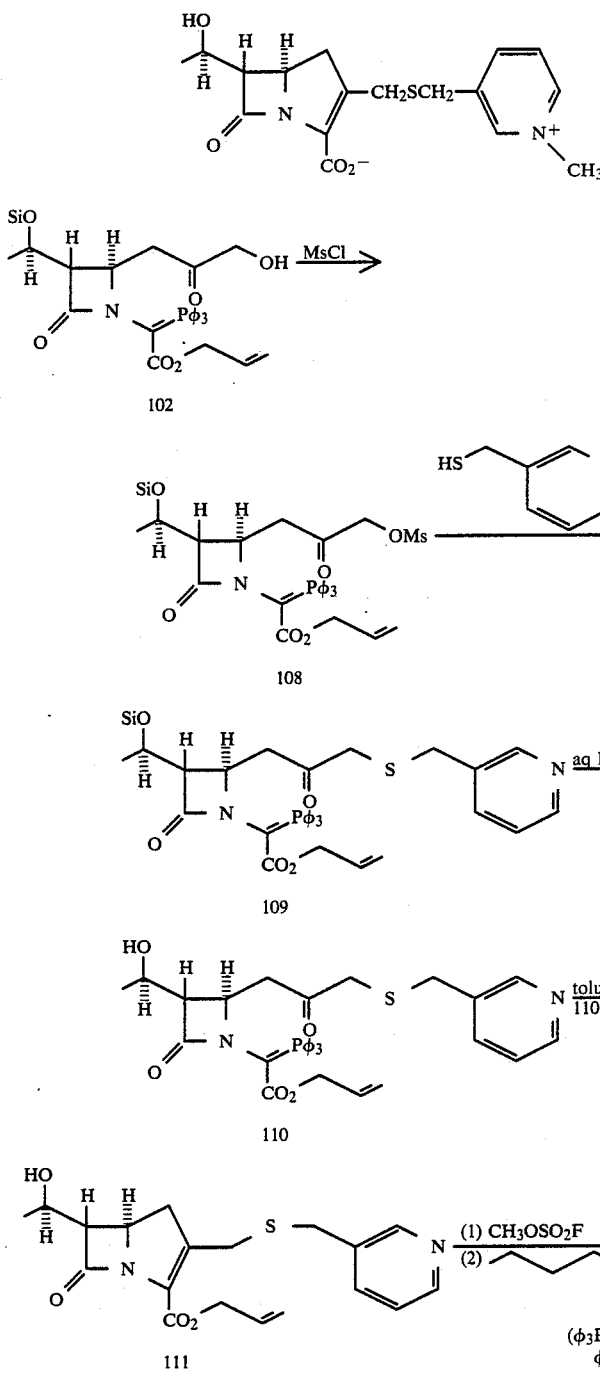

Triethylamine (56 mg, 0.55 mmol) and methanesulfonyl chloride (63 mg, 0.55 mmol) are added to a solution of hydroxymethylketone 102 (330 mg, 0.50 mmol) in anhydrous methylene chloride (2 ml) at 0° C. under dry nitrogen. After stirring for 30 min. the reaction mixture is added to brine (10 ml) and methylene chloride (20 ml) containing pH 7 phosphate buffer (2 ml of 0.5M). After phase separation, the aqueous layer is extracted with an additional portion of methylene chloride and the combined organics are washed with brine and dried over anhydrous magnesium sulfate. The dried organic phase is concentrated in vacuo and the residue is chromatographed on silica gel (eluting with 1:1 ethyl acetate/hexane) to provide mesylate 108.

Triethylamine (40 mg, 0.40 mmol) and 3-thiomethylpyridine (50 mg, 0.40 mmol) are added at 0° C. to a solution of mesylate 108 (280 mg, 0.38 mmol) in dry dimethylformamide (5 ml). The reaction mixture is allowed to warm to ambient temperature where it is aged for 2.5 hr. The reaction is then diluted with 1M dipotassium hydrogen phosphate (5 ml), brine (5 ml) and ethyl acetate (20 ml) and the layers are separated. The aqueous layer is extracted with an additional portion of ethyl acetate (8 ml) and the combined organics are washed with brine and dried over anhydrous magnesium sulfate. Removal of solvents in vacuo gives a gum which is chromatographed on silica gel (eluting with 1:1 ethyl acetate/hexane) to yield ketone 109.

Ketone 109 (192 mg, 0.25 mmol) is stirred under nitrogen at ambient temperature in a solution of 0.2M hydrochloric acid in 9:1 methanol/water (5 ml) for 6 hr. The reaction mixture is then added to 1M dipotassium hydrogen phosphate (5 ml), 1M potassium dihydrogen phosphate (5 ml), water and ethyl acetate (15 ml). After separation of the layers, the aqueous layer is extracted with an additional portion of ethyl acetate and the combined organics are washed with brine and dried over anhydrous magnesium sulfate. Solvents are removed in vacuo to yield a residue which is chromatographed on silica gel (eluting with ethyl acetate/methylene chloride) to yield carbinol 110.

A solution of ketocarbinol 110 (111 mg, 0.17 mmol) in deoxygenated toluene (4 ml) is heated at reflux under dry nitrogen for 6 hr., then concentrated in vacuo to give an oil. This material was chromatographed on silica gel preparative plates (eluting with ethyl acetate/methylene chloride) to provide carbapenem 111.

A solution of carbapenem 111 (41 mg, 0.11 mmol) in dry methylene chloride (4 ml) is cooled in an ice-water bath prior to the addition of methyl fluorosulfonate (14 mg, 0.12 mmol). The reaction mixture is stirred at 0° C. for 1 hr. during which time an oily precipitate forms. The methylene chloride is removed by decantation and the residue is washed with methylene chloride, subjected to high vacuum, then triturated with i-propanol and filtered. The resulting solid is added to methylene chloride (2 ml) and ethyl acetate (2 ml). To this mixture is added a solution of potassium ethyl hexanoate in ethyl acetate (0.22 ml of 0.5M, 0.11 mmol), tetrakis(triphenylphosphine)palladium (0.4 mg, 0.0003 mmol), and triphenyl phosphine (2 mg, 0.008 mmol). The resulting mixture is stirred at ambient temperature for 2.5 hr., then is concentrated in vacuo. The residue is partitioned between water and ethyl acetate. The aqueous layer is washed with an additional portion of ethyl acetate, then is concentrated and charged onto a column of Dowex 50W-X4 resin (sodium form, 200–400 mesh) which is eluted with water. Fractions containing the desired pyridinium product are pooled, concentrated, and lyophilized to provide product 112.

EXAMPLE 6

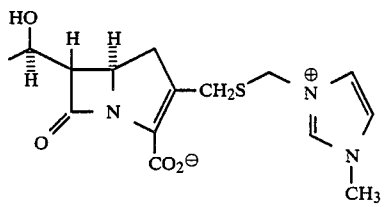

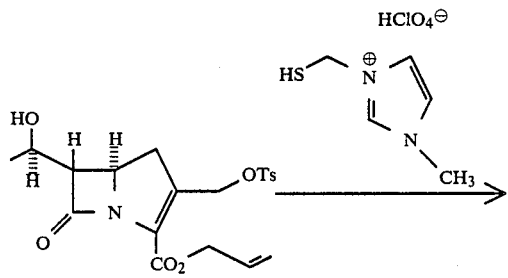

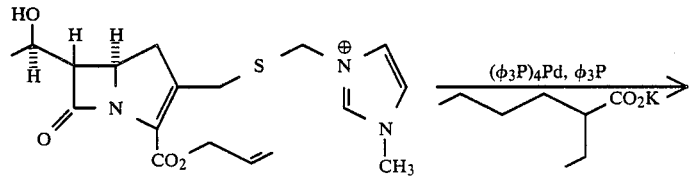

-continued

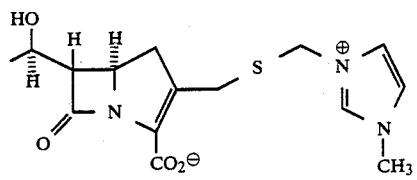

An ice cold solution of tosylate 105 (84 mg, 0.20 mmol) in anhydrous acetonitrile (5 ml) is treated with a solution of N-methyl-N'-mercaptomethylimidazolium perchlorate (48 mg, 0.21 mmol) in acetonitrile (0.25 ml) and with diisopropylethylamine (32 mg, 0.25 mmol). The mixture is stirred at 0° C. for 15 min., then is added to a suspension of celite in diethyl ether (10 ml) and stirred for 3 min. The celite is filtered off, washed with an additional portion of ether and extracted with 1:1 tetrahydrofuran/water. The extract is concentrated in vacuo lyophilized to give crude 113. This material is suspended in a mixture of methylene chloride (2 ml) and ethyl acetate (2 ml). To this mixture is added a solution of potassium ethylhexanoate in ethyl acetate (0.40 ml of 0.5M solution, 0.20 mmol), triphenylphosphine (3.4 mg, 0.014 mmol) and tetrakis(triphenylphosphine)palladium[0] (0.5 mg, 0.0005 mmol). The reaction mixture is stirred under nitrogen at ambient temperature for 2 hr., then is concentrated in vacuo. The residue is partitioned between water (5 ml) and ethyl ether (5 ml). The aqueous phase is separated and washed with an additional portion of ether, then is concentrated in vacuo and chromatographed on two RPS plates (eluting with ethanol/water). The U.V. active band is removed from the plates and extracted with 4:1 acetonitrile/water. This solution is washed four times with hexanes, then concentrated in vacuo and lyophilized to yield compound 114.

EXAMPLE 7

Preparation of:

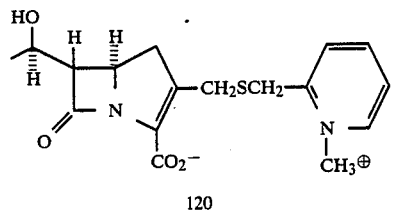

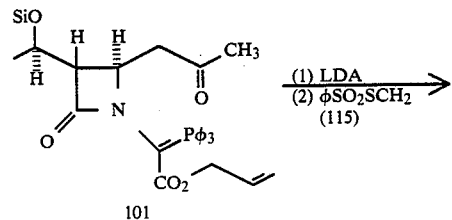

-continued

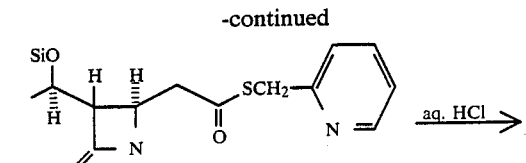

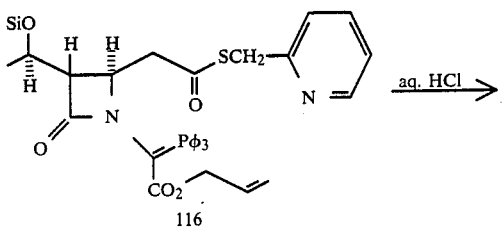

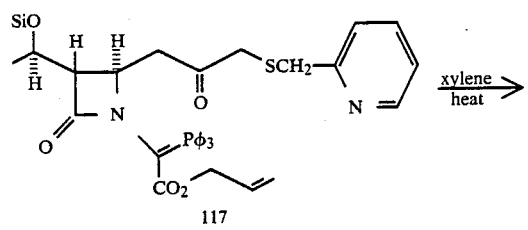

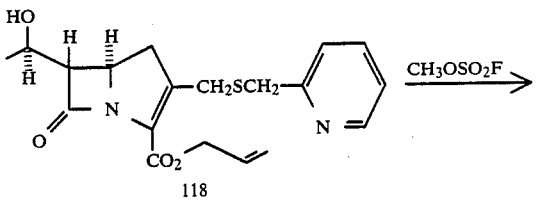

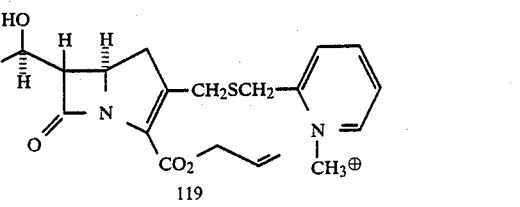

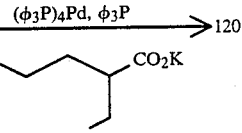

To a solution of diisopropylamine (159 mg, 1.6 mmol) in anhydrous tetrahydrofuran (15 ml) at 0° C. under dry nitrogen is added 2.2M n-butyllithium in hexane (0.727 ml, 1.6 mmol). After 10 min. the solution is cooled to −78° C. and a solution of methyl ketone 101 (965 mg, 1.5 mmol) in anhydrous tetrahydrofuran (2 ml) is added by syringe. The resulting solution is stirred at −78° C. for 10 min. then a solution of thiolsulfonate 115 (424 mg, 1.6 mmol) in anhydrous tetrahydrofuran (1 ml) is added by syringe. After an additional 30 min. the reaction is quenched by the addition of saturated aqueous ammonium chloride solution (5 ml) and the resulting mixture is poured into water (20 ml) and ethyl acetate (35 ml). The layers are separated and the aqueous layer is extracted with an additional portion of ethyl acetate (10 ml). The combined organics are dried over anhydrous magnesium sulfate and concentrated in vacuo. The resulting residue is chromatographed on silica gel (eluting with ethyl acetate/hexanes) to yield compound 116.

Ketone 116 (843 mg, 1.1 mmol) is stirred at ambient temperature in a solution of 0.2N hydrochloric acid in 9:1 methanol/water (16 ml) for 8 hr. The reaction mixture is then added to 1M dipotassium hydrogen phosphate (20 ml), 1M potassium dihydrogen phosphate (20 ml), water and ethyl acetate (50 ml). The layers are separated and the aqueous layer is extracted with an additional portion of ethyl acetate (15 ml). The combined organic layers are washed with brine, dried over magnesium sulfate and concentrated in vacuo to yield an oil. This material is chromatographed on silica gel (eluting with ethyl acetate/hexanes) to provide hydroxyketone 117.

A solution of hydroxyketone 117 (424 mg, 0.65 mmol) in deoxygenated xylene (13 ml) containing a trace of hydroquinone is heated at 130° under dry nitrogen for 7.5 hr. The reaction mixture is then cooled, concentrated in vacuo and the residue is chromatographed on silica gel (eluting with ethyl acetate/methylene chloride) to yield carbapenem 118.

A solution of carbapenem 118 (50 mg, 0.13 mmol) in dry methylene chloride (5 ml) is cooled in an ice-water bath prior to the addition of methyl fluorosulfonate (16 mg, 0.14 mmol). The reaction mixture is stirred at 0° C. for 1 hr. during which time an oily precipitate forms. The methylene chloride is removed by decantation and the residue is washed with methylene chloride, subjected to high vacuum, then triturated with i-propanol and filtered. The resulting solid which contains compound 119, is added to methylene chloride (2 ml) and ethyl acetate (2 ml). To this mixture is added a solution of potassium ethyl hexanoate in ethyl acetate (0.26 ml of 0.5M, 0.13 mmol), tetrakis(triphenylphosphine)palladium (0.4 mg, 0.0003 mmol), and triphenyl phosphine (2.4 mg, 0.009 mmol). The resulting mixture is stirred at ambient temperature for 2.5 hr., then is concentrated in vacuo. The residue is partitioned between water and ethyl acetate. The aqueous layer is washed with an additional portion of ethyl acetate, then is concentrated and charged onto a column of Dowex 50W-X4 resin (sodium form, 200–400 mesh) which is eluted with water. Fractions containing the desired pyridinium product are pooled, concentrated, and lyophilized to provide product 120.

EXAMPLE 8

Utilizing the procedures of Examples 4–7, the following internally alkylated compounds listed in Table II are prepared:

TABLE II

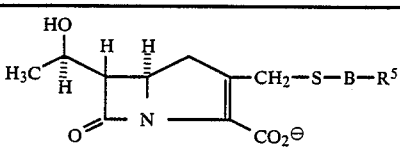

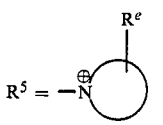

| B | R$^5$ |
|---|---|
| —CH$_2$CH$_2$— | 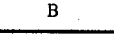 |
| —CH$_2$CH$_2$— | 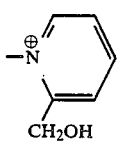 |
| —CH$_2$CH$_2$— | 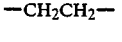 |
| —CH$_2$CH$_2$— | 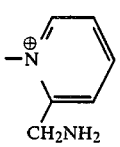 |
| —CH$_2$CH$_2$— |  |
| —CH$_2$CH$_2$— | 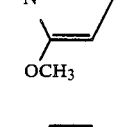 |
| —CH$_2$CH$_2$— |  |

TABLE II-continued

Structure:

HO−CH(CH₃)−[H,H]−β-lactam−CH₂−S−B−R⁵ with CO₂⁻ on the pyrroline ring $R^5 = -\overset{\oplus}{N}$ (ring with $R^e$)

or $-\overset{\oplus}{N}$ (ring with $R^e$)

| B | R⁵ |
|---|---|
| −CH₂CH₂− | −N⁺(pyridinium)−SO₃⁻ (2-position) |
| −CH₂CH₂− | −N⁺(pyridinium)−CH(OH)−SO₃⁻ (2-position) |
| −CH₂CH₂− | −N⁺(pyridinium)−N(CH₃)₂ |
| −CH₂CH₂− | −N⁺(pyridinium)−CH₃ |
| −CH₂CH₂− | −N⁺(pyridinium)−CH₂OH |
| −CH₂CH₂− | −N⁺(pyridinium)−CH₂NH₂ |
| −CH₂CH₂− | −N⁺(pyridinium)−CH₂−N(pyrrolidine) |
| −CH₂CH₂− | −N⁺(pyridinium)−CH₂CN |
| −CH₂CH₂− | −N⁺(pyridinium)−CH₂CO₂⁻ |
| −CH₂CH₂− | −N⁺(pyridinium)−CH₂CONH₂ |
| −CH₂CH₂− | −N⁺(pyridinium)−CH₂C(O)NHOH |
| −CH₂CH₂− | −N⁺(pyridinium)−CH₂CH₂SO₃⁻ |
| −CH₂CH₂− | −N⁺(pyridinium)−CH(OH)−SO₃⁻ (3-position) |
| −CH₂CH₂− | −N⁺(pyridinium)−CH₂SCH₃ |

TABLE II-continued

Structure (both columns 71 and 72):

$$\text{HO-CH(CH}_3\text{)-[carbapenem core with }\beta\text{-lactam]-CH}_2\text{-S-B-R}^5$$

with CO$_2^\ominus$ on the pyrroline ring.

$$R^5 = -\overset{\oplus}{N}\text{(ring)}-R^e \quad \text{or} \quad -N\text{(ring)}-R^e$$

| B | R⁵ (col 71) | B | R⁵ (col 72) |
|---|---|---|---|
| —CH₂CH₂— | 3-(CH₂S(O)CH₃)-pyridinium | —CH₂CH₂— | 3-(CH=N—OCH₃)-pyridinium |
| —CH₂CH₂— | 3-(CH₂SO₂CH₃)-pyridinium | —CH₂CH₂— | 3-(CONH₂)-pyridinium |
| —CH₂CH₂— | 3-CF₃-pyridinium | —CH₂CH₂— | 3-(C(O)NHOH)-pyridinium |
| —CH₂CH₂— | 3-(CH=CHCO₂⁻)-pyridinium | —CH₂CH₂— | 3-(CSNH₂)-pyridinium |
| —CH₂CH₂— | 3-CN-pyridinium | —CH₂CH₂— | 3-Cl-pyridinium |
| —CH₂CH₂— | 3-(CH₂N(CH₃)₂)-pyridinium | —CH₂CH₂— | 3-F-pyridinium |
| —CH₂CH₂— | 3-(CH=N—OH)-pyridinium | —CH₂CH₂— | 3-NH₂-pyridinium |

TABLE II-continued

| | | | | |
|---|---|---|---|---|
| | (structure with $R^5$) | | | (structure with $R^5$) |
| | $R^5 = $ (ring with $R^e$) | | | $R^5 = $ (ring with $R^e$) |
| B | | | B | |
| $-CH_2CH_2-$ | pyridinium-4-SCH$_3$ | | $-CH_2CH_2-$ | pyridinium-4-CH$_2$CN |
| $-CH_2CH_2-$ | pyridinium-3-SCH$_2$CO$_2^\ominus$ | | $-CH_2CH_2-$ | pyridinium-4-CH$_2$CONH$_2$ |
| $-CH_2CH_2-$ | pyridinium-3-SO$_3^\ominus$ | | $-CH_2CH_2-$ | pyridinium-4-CH$_2$C(O)NHOH |
| $-CH_2CH_2-$ | pyridinium-4-CH$_2$-tetrazole | | $-CH_2CH_2-$ | pyridinium-4-CH$_2$CH$_2$CO$_2^\ominus$ |
| $-CH_2CH_2-$ | pyridinium-4-CH$_3$ | | $-CH_2CH_2-$ | pyridinium-4-CH$_2$-tetrazole |
| $-CH_2CH_2-$ | pyridinium-4-CH$_2$OH | | $-CH_2CH_2-$ | pyridinium-4-CH$_2$CH$_2$SO$_3^\ominus$ |
| $-CH_2CH_2-$ | pyridinium-4-CH(OCH$_2$CH$_2$O) (dioxolane) | | $-CH_2CH_2-$ | pyridinium-4-CH=N-OH |
| $-CH_2CH_2-$ | pyridinium-4-CH(OH)(SO$_3^\ominus$) | | $-CH_2CH_2-$ | pyridinium-4-CH=N-OCH$_3$ |
| | | | $-CH_2CH_2-$ | pyridinium-4-CO$_2^\ominus$ |
| | | | $-CH_2CH_2-$ | pyridinium-4-CONH$_2$ |

TABLE II-continued

Core structure (both columns 75 and 76):

Carbapenem with (R)-1-hydroxyethyl group: HO-CH(CH₃)-CH- attached to β-lactam, with -CH₂-S-B-R⁵ side chain and CO₂⁻.

$R^5 = $ cyclic ammonium $-\overset{\oplus}{N}$-ring with $R^e$ substituent, or $-\overset{\oplus}{N}$-fused ring with $R^e$.

| B | (column 75) | B | (column 76) |
|---|---|---|---|
| —CH₂CH₂— | $-\overset{\oplus}{N}$-pyridyl-4-C(O)NHOH | —CH₂CH₂— | pyrazinium with 3-N(CH₃)₂ |
| —CH₂CH₂— | $-\overset{\oplus}{N}$-pyridyl-4-CSNH₂ | —CH₂CH₂— | pyrazinium with CONH₂ |
| —CH₂CH₂— | $-\overset{\oplus}{N}$-pyridyl-4-CN | —CH₂CH₂— | pyrazinium with CO₂⁻ |
| —CH₂CH₂— | $-\overset{\oplus}{N}$-pyridyl-4-OCH₃ | —CH₂CH₂— | pyridazinium |
| —CH₂CH₂— | $-\overset{\oplus}{N}$-pyridyl-4-SCH₃ | —CH₂CH₂— | pyrimidinium with OCH₃ |
| —CH₂CH₂— | $-\overset{\oplus}{N}$-pyridyl-4-SCH₂CO₂⁻ | —CH₂CH₂— | N-methylpyrazolium |
| —CH₂CH₂— | $-\overset{\oplus}{N}$-pyridyl-4-SONH₂ | —CH₂CH₂— | N-methyl-1,2,3-triazolium |
| —CH₂CH₂— | $-\overset{+}{N}$-pyridyl-3-CONH₂,4-CO₂⁻ | —CH₂CH₂— | N-methylimidazolium |
| —CH₂CH₂— | pyrazinium | —CH₂CH₂— | thiazolium |

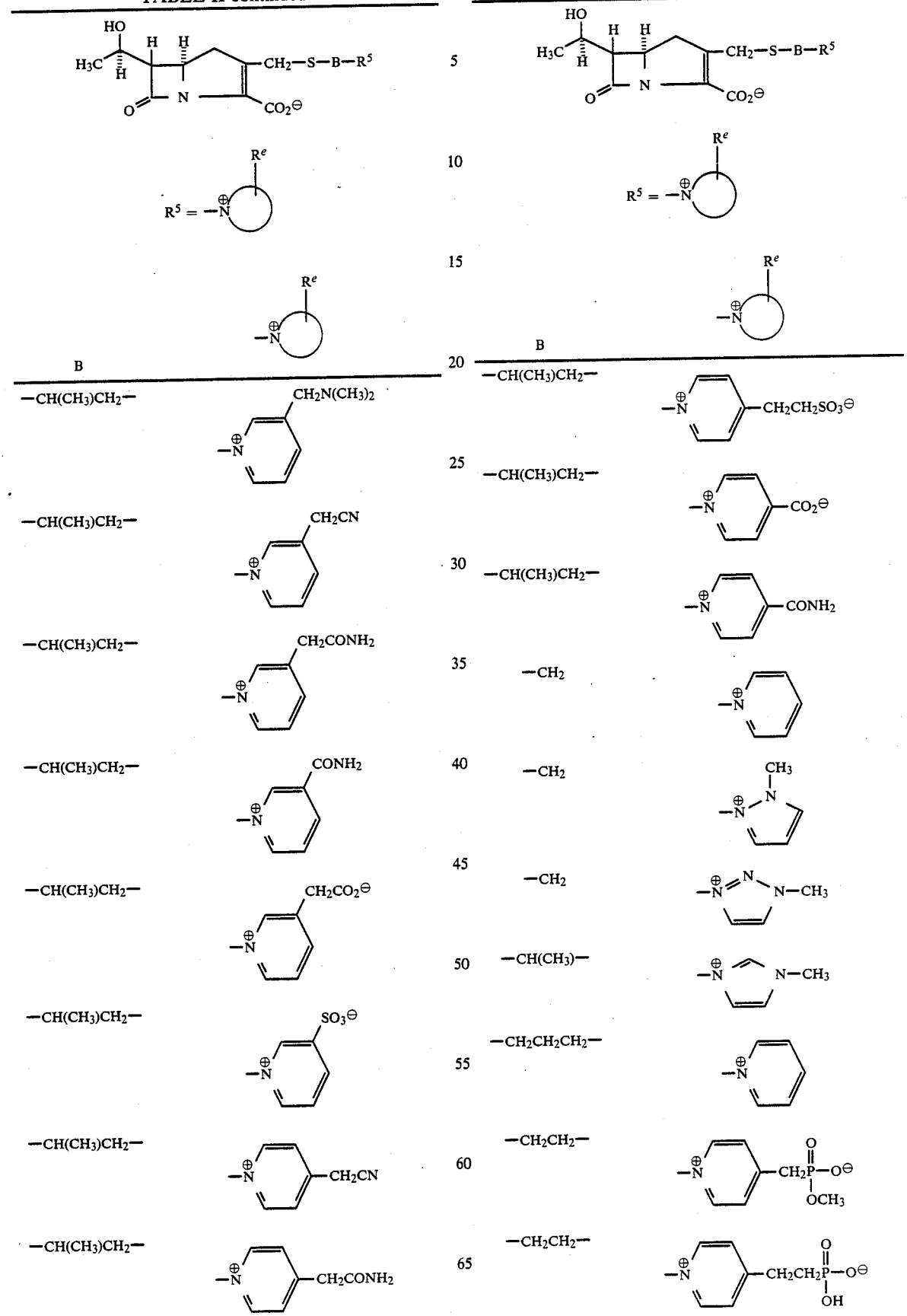

TABLE II-continued (Chemical structures showing carbapenem compounds with hydroxyethyl substituent and $CH_2$-S-B-$R^5$ side chain, where $R^5$ represents quaternary ammonium heterocycles with $R^e$ substituent.)

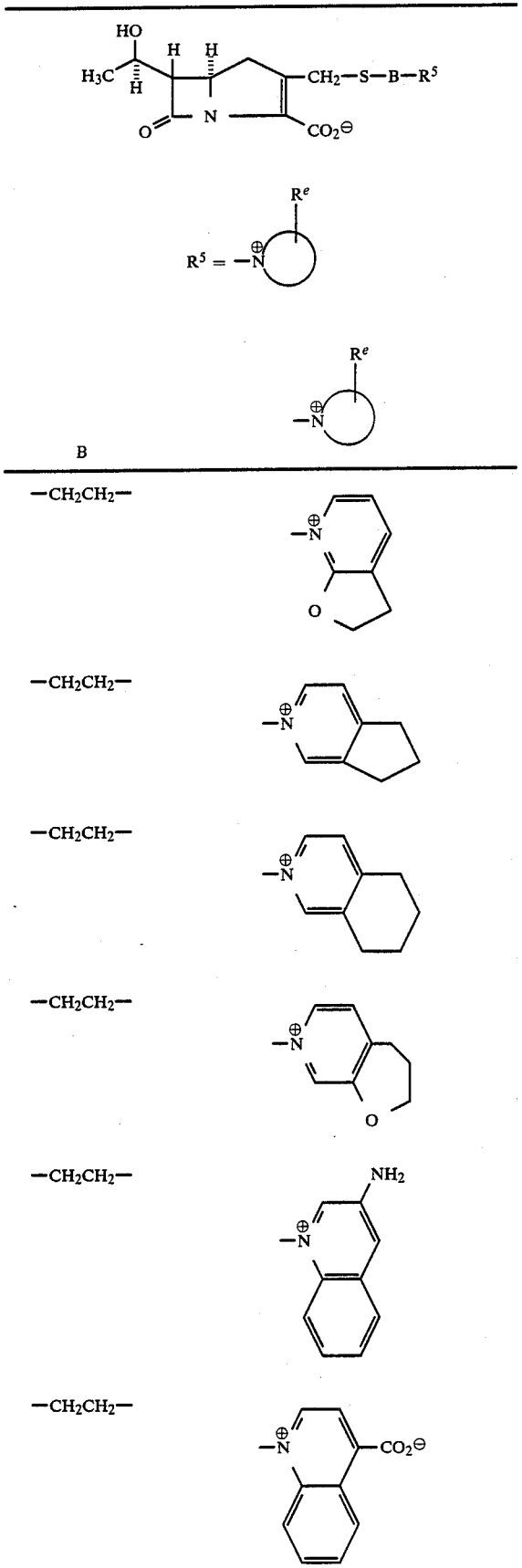
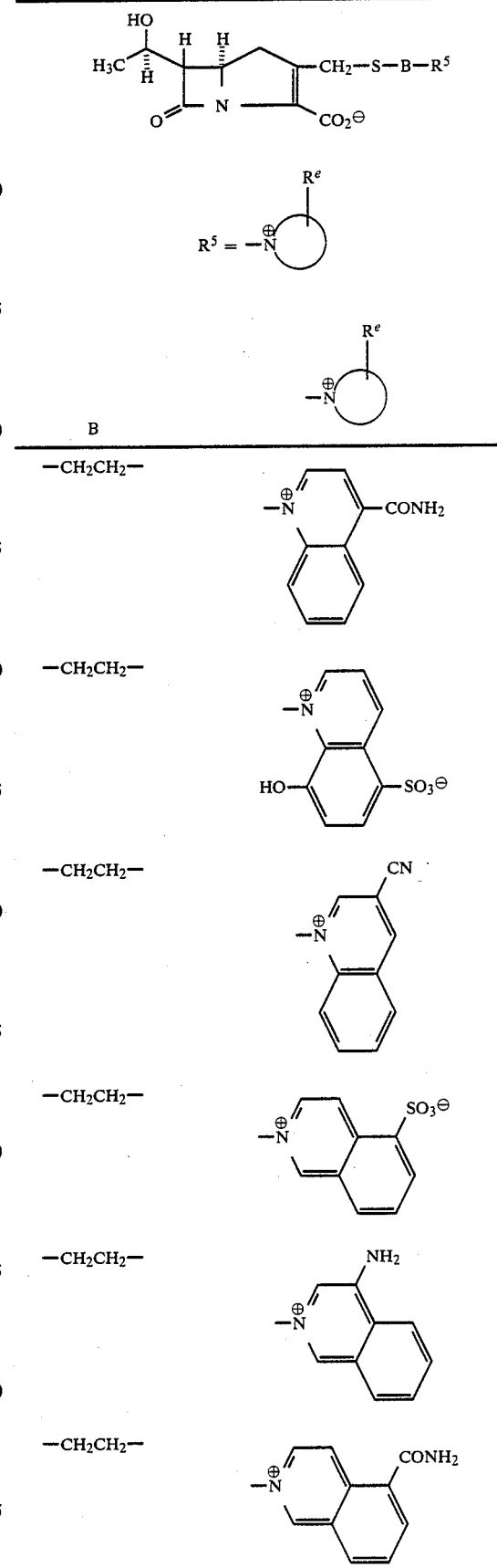

TABLE II-continued

[Structure: carbapenem core with HO-H₃C-CH(H)- group, H, bicyclic β-lactam with N, O=, CO₂⁻, and CH₂—S—B—R⁵ side chain]

$$R^5 = -\overset{\oplus}{N}\begin{pmatrix}R^e\end{pmatrix}$$

| B | |
|---|---|
| —CH₂CH₂— | isoquinolinium with CONH₂ |
| —CH₂CH₂— | isoquinolinium with CO₂⁻ |
| —CH₂CH₂— | 1,5-naphthyridinium |
| —CH₂CH₂— | quinoxalinium |
| —CH₂CH₂— | thieno-pyridinium |
| —CH₂CH₂— | thieno-pyridinium |
| —CH₂CH₂— | thieno-pyridinium with CO₂⁻ |
| —CH₂CH₂— | furo-pyridinium |
| —CH₂CH₂— | furo-pyridinium |
| —CH₂CH₂— | thieno-pyridinium with CO₂⁻ |
| —CH₂CH₂— | thieno-pyridinium with NH₂ |
| —CH₂CH₂— | pyrrolo-pyridinium (HN) |
| —CH₂CH₂— | imidazolium fused cyclohexane, N—CH₃ |

TABLE II-continued

Structure: A carbapenem with HO-CH(CH₃)- substituent, β-lactam ring fused to pyrroline with CH₂—S—B—R⁵ group and CO₂⁻

$$R^5 = -\overset{\oplus}{N}\!\!\underset{R^e}{\diagup}\bigcirc$$

$$-\overset{\oplus}{N}\!\!\underset{R^e}{\diagup}\bigcirc$$

| B | R⁵ ring systems |
|---|---|
| —CH₂CH₂— | N-methyl benzimidazolium (⊕N=CH–N–CH₃ fused to benzene) |
| —CH₂CH₂— | 2,3,4,6,7,8-hexahydropyrido[1,2-a]pyrimidinium |
| —CH₂CH₂— | 6,7-dihydro-5H-pyrrolo[1,2-a]imidazolium |
| —CH₂CH₂— | benzothiazolium |
| —CH₂CH₂— | 4,5,6,7-tetrahydro-1,2,3-benzotriazinium |
| —CH₂CH₂— | 1-methyl-4,5,6,7-tetrahydro-1,2,3-benzotriazolium |
| —CH₂CH₂— | 1-methylindazolium |
| —CH₂CH₂— | thieno[2,3-d]pyridazinium |
| —CH₂CH₂— | tetrazolo[1,5-b]pyridazinium |
| —CH₂CH₂— | tetrazolo[1,5-b]pyridazinium-carboxylate (CO₂⁻) |
| —CH₂CH₂— | tetrazolo[1,5-a]pyrimidinium |
| —CH₂CH₂— | tetrazolo[1,5-a]pyrimidinium-carboxylate (CO₂⁻) |
| —CH₂CH₂— | 6,7-dihydro-5H-cyclopenta[b]pyridinium |

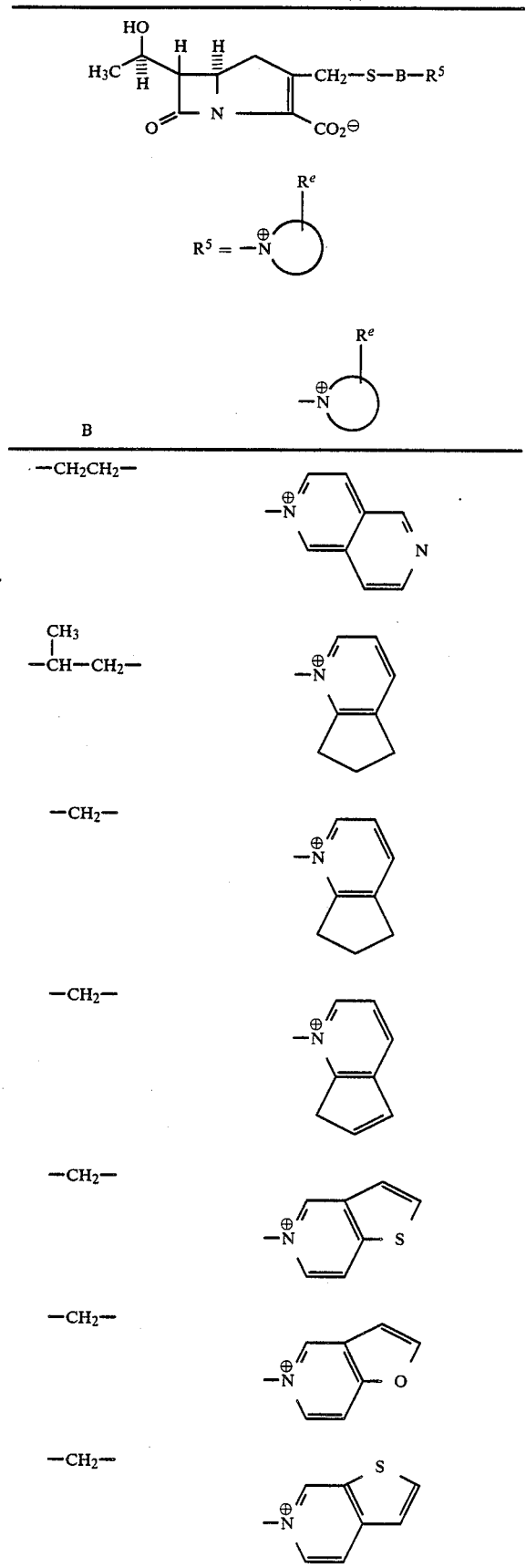
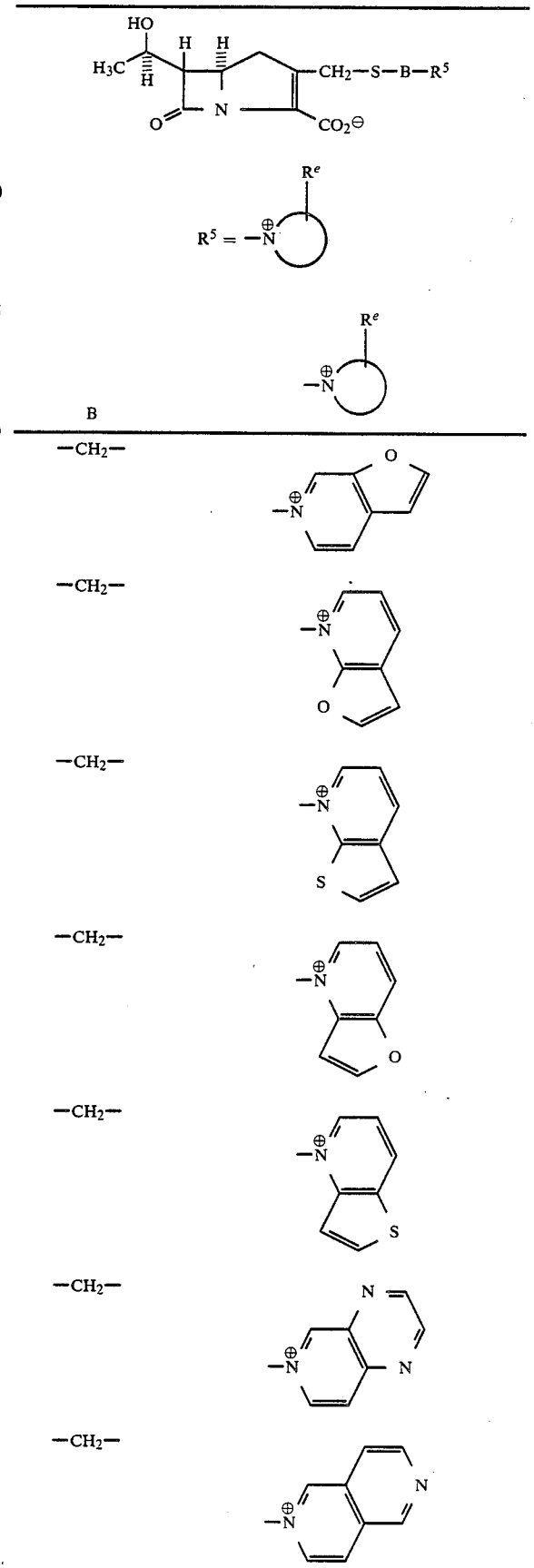

TABLE II-continued (structures shown)

TABLE II-continued
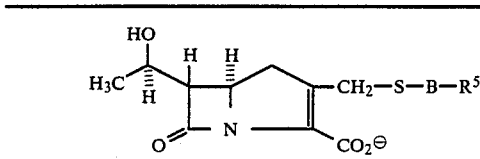
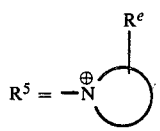
| B | |
|---|---|
| —CH₂CH₂— | 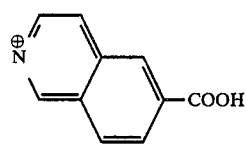 |
| —CH₂CH₂— | 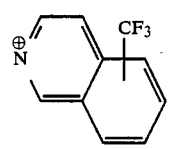 |
| —CH₂CH₂— | 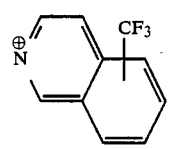 |
| —CH(CH₃)CH₂— | 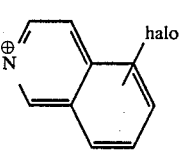 |
| —CH(CH₃)CH₂— | 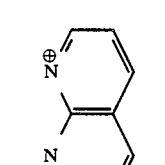 |
| —CH(CH₃)CH₂— | 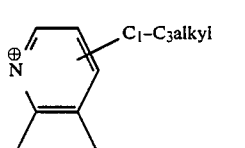 |
TABLE II-continued
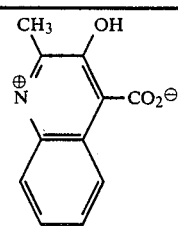
| B | |
|---|---|
| —CH(CH₃)CH₂— | 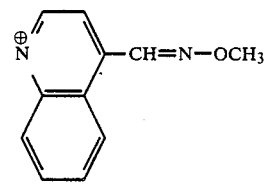 |
| —CH(CH₃)CH₂— | 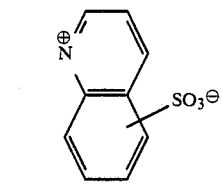 |
| —CH(CH₃)CH₂— | 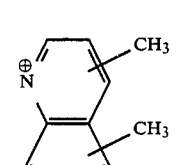 |
| —CH(CH₃)CH₂— | 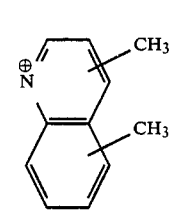 |
What is claimed is:
1. A compound having the formula:
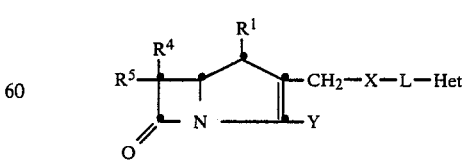 (I.)
wherein:
$R^1$ is hydrogen,
$R^4$ and $R^5$ are independently H, CH$_3$—, CH$_3$CH$_2$—, (CH$_3$)$_2$CH—, HOCH$_2$—, CH$_3$CH(OH)—, $(CH_3)_2C(OH)$—, $FCH_2$, $F_2CH$—, $F_3C$—, $CH_3CH(F)$—, $CH_3CF_2$—, or $(CH_3)_2C(F)$—;

X is —S—, —SO—, —SO$_2$—, —O— or —NH—;

L is a bridging group comprising substituted or unsubstituted $C_1$-$C_4$ straight, $C_2$-$C_6$ branched or $C_3$-$C_7$ cycloalkyl groups wherein the substituents are selected from $C_1$-$C_6$ alkyl, O—$C_1$-$C_6$ alkyl, S—$C_1$-$C_6$ alkyl, $CF_3$, $N(C_1$-$C_6$ alkyl$)_2$;

Het is a mono- or bicyclic heteroarylium group containing from 5-11 ring atoms of which up to 5 are heteroatoms, in addition to the quaternary nitrogen, being of the formula:

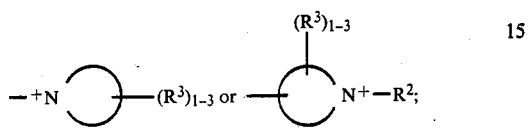

wherein:

$R^2$ is (1) an unsubstituted or substituted $C_1$-$C_6$ alkyl radical;

(2) an unsubstituted or substituted $C_2$-$C_6$ alkenyl radical;

(3) an unsubstituted or substituted $C_2$-$C_6$ alkynyl radical;

(4) a $C_3$-$C_7$ cycloalkyl radical in which the ring is substituted or unsubstituted and one or more atoms may be replaced by a heteroatom;

(5) a $C_3$-$C_7$ cycloalkyl methyl radical in which the ring may be substituted and one or more atoms may be replaced by a heteroatom;

(6) an unsubstituted or substituted $C_5$-$C_7$ cycloalkenyl radical;

(7) an unsubstituted or substituted bivalent $C_2$-$C_6$ alkyidene radical, optionally interrupted by a heteroatom, and joined to the heteroarylium group to form a ring which is carbocyclic or in which one or more atoms is replaced by a heteroatom and wherein the new ring may contain one or more double bonds;

(8) an unsubstituted or substituted phenyl or heteroaryl radical;

(9) an unsubstituted or substituted phenyl ($C_1$-$C_4$ alkyl) or heteroaryl ($C_1$-$C_4$ alkyl) radical;

(10) a cyano ($C_1$-$C_4$ alkyl) radical;

(11) a carboxy ($C_1$-$C_4$ alkyl) radical;

(12) a sulfo ($C_1$-$C_4$ alkyl) radical;

(13) a carbamoyl ($C_1$-$C_4$ alkyl) radical;

(14) a phosphonyl ($C_1$-$C_4$ alkyl) radical;

(15) a hydroxy ($C_1$-$C_4$ alkyl) radical; or

(16) an amino ($C_1$-$C_4$ alkyl) radical in which the nitrogen atom is unsubstituted or substituted with one to three $C_1$-$C_4$ alkyl groups;

wherein the substituents in the above definitions of $R^2$ are independently selected from the group consisting of:

(a) a trifluoromethyl group;

(b) a halogen atom;

(c) an unsubstituted or substituted $C_1$-$C_4$ alkoxyl radical;

(d) a hydroxy group;

(e) an unsubstituted or substituted ($C_1$-$C_6$ alkyl) carbonyloxy radical;

(f) a carbamoyloxy radical which is unsubstituted or substituted on nitrogen with one or two $C_1$-$C_4$ alkyl groups;

(g) a $C_1$-$C_6$ alkylthio radical, $C_1$-$C_6$ alkylsulfinyl radical or $C_1$-$C_6$ alkylsulfonyl radical, each of which is unsubstituted or substituted on the alkyl group;

(h) a sulfo group;

(i) a sulfamoyl group which is unsubstituted or substituted on nitrogen by one or two $C_1$-$C_4$ alkyl groups;

(ia) an amino group;

(ib) a mono ($C_1$-$C_4$ alkyl) amino or di($C_1$-$C_4$ alkyl)amino group, each of which is unsubstituted or unsubstituted on the alkyl group;

(j) a formylamino group;

(k) an unsubstituted or substituted ($C_1$-$C_6$alkyl)carbonylamino radical;

(l) a ($C_1$-$C_4$alkoxyl) carbonylamino radical;

(m) a ureido group in which the terminal nitrogen is unsubstituted or substituted with one or two $C_1$-$C_4$ alkyl groups;

(n) an arylsulfonamido or a ($C_1$-$C_6$ alkyl) sulfonamido group;

(o) a cyano group;

(p) a formyl or acetalized formyl radical;

(q) an unsubstituted or substituted ($C_1$-$C_6$ alkyl)carbonyl radical wherein the carbonyl is free or acetalized;

(r) an unsubstituted or substituted phenylcarbonyl or heteroarylcarbonyl radical;

(ra) a hydroximinomethyl radical in which the oxygen or carbon atom is optionally substituted by a $C_1$-$C_4$ alkyl group;

(s) a carboxyl group;

(t) a ($C_1$-$C_6$alkoxy)carbonyl radical;

(u) a carbamoyl radical which is unsubstituted or substituted on nitrogen by one or two $C_1$-$C_4$ alkyl groups;

(v) an N-hydroxycarbamoyl or N($C_1$-$C_4$ alkoxy)carbamoyl radical in which the nitrogen atom may be additionally substituted by a $C_1$-$C_4$ alkyl group;

(w) a thiocarbamoyl group;

(x) a 5-(1H)-tetrazolyl group;

(xa) an amidino group

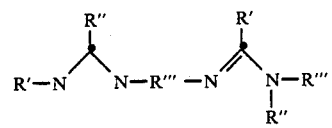

where R', R'' and R''' are independently hydrogen, $C_1$-$C_4$ alkyl or wherein two of the alkyl groups together form a $C_2$-$C_6$ alkylidene radical optionally interrupted by a heteroatom and joined together to form a ring;

(xb) a carboxamidino group

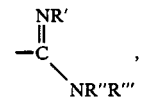

where R', R'' and R''' are defined above;

(xc) a guanidinyl group where R'' in (ab) above is $NR^{iv}R^v$ and $R^{iv}$ and $R^v$ are as defined for R' through R'''' above;

(y) a phosphonate group —P(O)(OH)OR' where R' is $C_1$-$C_3$ alkyl;

(z) an alkyl phosphonate group —$(CH_2)_n$P(O)(OH)(OR') where n=1 to 3 and R' is $C_1$-$C_3$ alkyl;

(aa) hydrogen;

(ab) an unsubstituted or substituted $C_1$-$C_6$ alkyl radical;

(ac) an unsubstituted or substituted $C_2$-$C_6$ alkenyl radical;

(ad) an unsubstituted or substituted $C_2$-$C_6$ alkynyl radical;

(ae) a $C_3$-$C_7$ cycloalkyl radical in which the ring is substituted or unsubstituted and one or more atoms may be replaced by a heteroatom;

(af) a $C_3$-$C_7$ cycloalkyl methyl radical in which the ring may be substituted and one or more atoms may be replaced by a heteroatom;

(ag) an unsubstituted or substituted $C_5$-$C_7$ cycloalkenyl radical;

(ah) an unsubstituted or substituted phenyl or heteroaryl radical; and (ai) an unsubstituted or substituted phenyl ($C_1$-$C_4$ alkyl) or heteroaryl ($C_1$-$C_4$ alkyl) radical; and (a) hydrogen;

(b) an unsubstituted or substituted $C_1$-$C_6$ alkyl radical;

(c) an unsubstituted or substituted $C_2$-$C_6$ alkenyl radical;

(d) an unsubstituted or substituted $C_2$-$C_6$ alkynyl radical;

(e) a $C_3$-$C_7$ cycloalkyl radical in which the ring is substituted or unsubstituted and one or more atoms may be replaced by a heteroatom;

(f) a $C_3$-$C_7$ cycloalkyl methyl radical in which the ring may be substituted and one or more atoms may be replaced by a heteroatom;

(g) an unsubstituted or substituted $C_5$-$C_7$ cycloalkenyl radical;

(h) an unsubstituted or substituted phenyl or heteroaryl radical;

(i) an unsubstituted or substituted phenyl ($C_1$-$C_4$ alkyl) or heteroaryl ($C_1$-$C_4$ alkyl) radical; and (j) a trifluoromethyl group;

(k) a halogen atom;

(l) an unsubstituted or substituted $C_1$-$C_4$ alkoxyl radical;

(m) a $C_1$-$C_6$ alkylthio radical, $C_1$-$C_6$ alkylsulfinyl radical or $C_1$-$C_6$ alkylsulfonyl radical, each of which is unsubstituted or substituted on the alkyl group;

(n) a mono ($C_1$-$C_4$ alkyl) amino or di($C_1$-$C_4$ alkyl)amino group, each of which is unsubstituted or substituted on the alkyl group; or (o) a cyano group; and (i) COOH or a pharmaceutically acceptable ester or salt thereof, (ii) COOR wherein R is a removable carboxy protecting group, (iii) COOM wherein M is an alkali metal, or (iv) COO$^-$; provided that when Y is other than (iv) a counterion $Z^-$ is provided.

2. A compound of claim 1 wherein $R^1$ is hydrogen.

3. A compound of claim 1 wherein L is substituted or unsubstituted branched or linear $C_1$-$C_4$ alkyl.

4. A compound of claim 3 wherein L is —$CH_2$—, —$CH(CH_3)$—, —$(CH_2)_2$—, or —$CH(CH_3)CH_2$—.

5. A compound of claim 1 wherein Het is monocyclic heteroarylium having 5-6 ring atoms.

6. A compound of claim 5 wherein Het is a pyridinium, diazolium, triazolium, thiazolium or oxazolium group.

7. A compound of claim 1 wherein $R^2$ is an unsubstituted or substituted $C_1$-$C_6$ alkyl group, carboxy ($C_1$-$C_4$ alkyl), carbamoyl ($C_1$-$C_4$ alkyl), sulfo ($C_1$-$C_4$ alkyl), heteroaryl ($C_1$-$C_4$ alkyl), or cyano ($C_1$-$C_4$ alkyl).

8. A compound of claim 1 wherein $R^3$ is hydrogen, N($C_1$-$C_3$ alkyl), O—$C_1$-$C_4$ alkyl, $C_1$-$C_4$ alkyl, CN, $CF_3$ or $CH_2OH$.

9. A compound of claim 1 wherein the compound is a member selected from the group wherein $R^1$ is H and

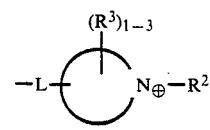

is selected from

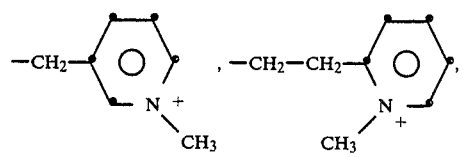

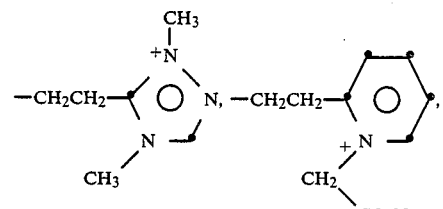

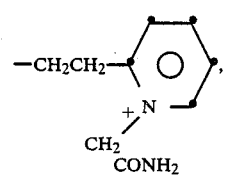

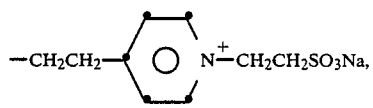

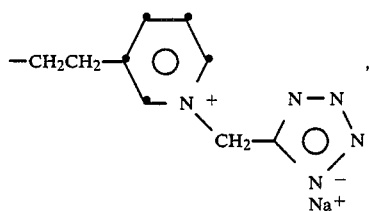

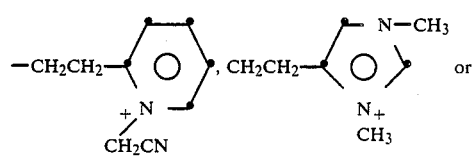

-continued

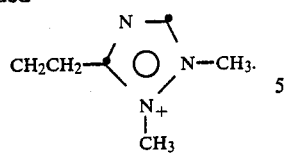

10. A compound of claim 1 wherein

is monocyclic.

11. The compound of claim 10 wherein L is unsubstituted or substituted $C_1$-$C_6$ alkyl wherein the substituents are $NH_2$, $CF_3$, OH or $C_1$-$C_4$ alkoxy, CN, or $CONH_2$.

12. The compound of claim 10 wherein the $-N^+$ group is a substituted or unsubstituted pyridinium, pyridazinium, pyrimidinium, pyrazinium, pyrazolium, imidazolium or triazolium.

13. The compound of claim 12 wherein the $-N^{30}$ group is substituted or unsubstituted pyridinium or pyrazinium, wherein the substituent is $NH_2$, OH, $CH=N-OCH_3$, $C_1$-$C_3$ alkyl, $CF_3$, $CONH_2$, COOH, halo, $C_1$-$C_3$alkoxy, $SO_3H$, CHO, CN,

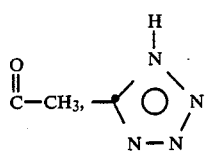

$N(C_1$-$C_3$alkyl$)_2$, $NH(C_1$-$C_3$alkyl), $CH_2CO_2H$, $CH_2SO_3H$, $CH_2OH$, $CH_2CN$, $CH_2CONH_2$, or $CH_2N(C_1$-$C_3$alkyl$)_2$.

14. The compound of claim 11 wherein L is $-CH_2-$, $-CH_2-CH_2-$ or $$-CH-CH_2-$$
$$\phantom{-}|$$
$$\phantom{-}CH_3$$

15. The compound of claim 14 wherein

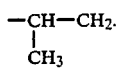

is substituted or unsubstituted pyridinium.

16. The compound of claim 15 wherein said

group is pyridinium, carboxypyridinium, hydroxypyridinium, $C_1$-$C_3$ alkylpyridinium or di$C_1$-$C_3$alkylaminopyridinium.

17. The compound of claim 16 wherein L is $-(CH_2)_2-$ or $-CH(CH_3)-CH_2-$.

18. The compound of claim 17 wherein Y is (iv) and

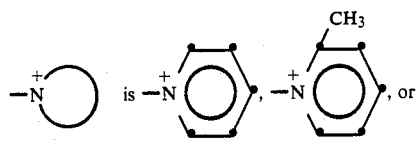

19. The compound of claim 18 wherein

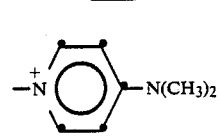

20. The compound of claim 17 wherein Y is (iii) and

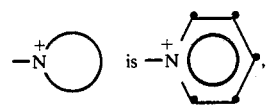

21. The compound of claim 20 wherein

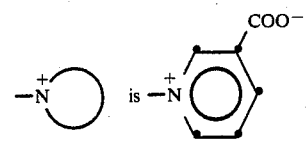

22. A compound of claim 1 having the sterochemical configuration:

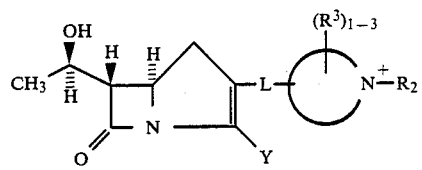

23. The combination of a compound of claim 1 and a DHP inhibitor.

24. The combination of claim 13 wherein the DHP inhibitor is 7-(L-2-amino-2-carboxyethylthio)-2-(2,2-dimethylcyclopropanecarboxamido)-2-heptenoic acid.

25. A pharmaceutical composition for antibiotic use comprising an antibacterially effective amount of a compound of claim 1, an inhibitorily effective amount of a DHP inhibitor, and, optionally, a pharmaceutically acceptable carrier.

26. A pharmaceutical composition according to claim 14 wherein the DHP inhibitor is 7-(L-2-amino-2-carboxyethylthio)-2-(2,2-dimethylcyclopropanecarboxyamido)-2-heptenoic acid.

27. A method of treating bacterial infections in human or animal subjects in need of such treatment comprising coadministering to said subjects an antibacterially effective amount of a compound of claim 1, an inhibitorily effective amount of a DHP inhibitor.

28. A method according to claim 27 wherein the DHP inhibitor is 7-(L-2-amino2-carboxyethylthio)-2-(2,2-dimethylcyclopropanecarboxamido)-2-heptenoic acid.

29. A pharmaceutical composition for antibiotic use comprising an antibacterially effective amount of a compound of claim 1, and, optionally, a pharmaceutically acceptable carrier.

30. A method of treating bacterial infections in human or animal subjects in need of such treatment comprising administering to said subjects an antibacterially effective amount of a compound of claim 1.

* * * * *